United States Patent
van Dam et al.

(10) Patent No.: US 11,660,571 B2
(45) Date of Patent: May 30, 2023

(54) MICROSCALE DEVICE AND METHOD FOR PURIFICATION OF RADIOPHARMACEUTICALS

(71) Applicant: THE REGENTS OF THE UNIVERSITY OF CALIFORNIA, Oakland, CA (US)

(72) Inventors: R. Michael van Dam, Sherman Oaks, CA (US); Noel S. Ha, Los Angeles, CA (US); Jason Jones, Los Angeles, CA (US); Jimmy Ly, San Francisco, CA (US); Stephen Liu, Los Angeles, CA (US); Shilin Cheung, North Hills, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 474 days.

(21) Appl. No.: 16/461,272

(22) PCT Filed: Nov. 14, 2017

(86) PCT No.: PCT/US2017/061611
§ 371 (c)(1),
(2) Date: May 15, 2019

(87) PCT Pub. No.: WO2018/093794
PCT Pub. Date: May 24, 2018

(65) Prior Publication Data
US 2020/0147548 A1 May 14, 2020

Related U.S. Application Data

(60) Provisional application No. 62/423,963, filed on Nov. 18, 2016.

(51) Int. Cl.
*B01D 57/02* (2006.01)
*G01N 27/447* (2006.01)
(Continued)

(52) U.S. Cl.
CPC .............. *B01D 57/02* (2013.01); *A61K 51/00* (2013.01); *B01L 3/502715* (2013.01);
(Continued)

(58) Field of Classification Search
CPC ....... G01N 27/44717; G01N 27/44721; G01N 27/44743; G01N 27/44791; G01N 27/447;
(Continued)

(56) References Cited

U.S. PATENT DOCUMENTS 6,270,641 B1 * 8/2001 Griffiths ........... G01N 27/44791
204/600
9,291,606 B2 3/2016 Hansteen et al.
(Continued)

FOREIGN PATENT DOCUMENTS

WO  WO 02/43615 A2   6/2002
WO  WO 2016/063072    4/2016
WO  WO 2018/067976 A1 10/2017

OTHER PUBLICATIONS

Cheung et al., The separation and detection of PET tracers via capillary electrophoresis for chemical identity and purity analysis, Journal of Pharmaceutical and Biomedical Analysis, vol. 94, pp. 12-18 (2014) (Year: 2014).*
(Continued)

*Primary Examiner* — Joshua L Allen
*Assistant Examiner* — Vivian A Tran
(74) *Attorney, Agent, or Firm* — Vista IP Law Group LLP

(57) ABSTRACT

A microfluidic chip device for the purification of radiochemical compounds includes a chip having an injection
(Continued)

channel and intersecting branch channels with a plurality of valves are located along the injection channel and branch channels and configured to retain a plug of solution containing the radiochemical compound. The chip further includes a serpentine channel segment (for separation) coupled to the output of the injection channel. A high voltage power source advances the plug of solution through the purification region and into the downstream fraction collection channel. The chip includes a downstream fraction collection channel coupled to the serpentine channel segment and having an optical and radiation detection regions. One or more branch fraction channels intersect with the fraction collection channel and include valves located therein so that the radiochemical compound that is detected using a radiation detector is directed into the desired branch fraction channel for subsequent use.

8 Claims, 12 Drawing Sheets

(51) Int. Cl.
  *A61K 51/00* (2006.01)
  *B01L 3/00* (2006.01)
(52) U.S. Cl.
  CPC .. *B01L 3/502738* (2013.01); *G01N 27/44717* (2013.01); *G01N 27/44721* (2013.01); *G01N 27/44743* (2013.01); *G01N 27/44791* (2013.01)
(58) Field of Classification Search
  CPC .. G01N 27/44704; B01D 57/02; A61K 51/00; B01L 3/502715; B01L 3/502738
  See application file for complete search history.

(56) References Cited

U.S. PATENT DOCUMENTS

| | | | |
|---|---|---|---|
| 2002/0110926 A1 | 8/2002 | Kopf-Sill et al. | |
| 2002/0119482 A1* | 8/2002 | Nelson | B01L 3/502761 435/6.19 |
| 2004/0115838 A1* | 6/2004 | Quake | B01F 13/1022 436/538 |
| 2005/0232387 A1* | 10/2005 | Padgett | A61K 51/0491 376/194 |
| 2005/0232861 A1 | 10/2005 | Buchanan et al. | |
| 2008/0064110 A1* | 3/2008 | Elizarov | C07B 59/00 436/43 |
| 2009/0253181 A1 | 10/2009 | Vangbo et al. | |
| 2009/0302228 A1* | 12/2009 | Hadjioannou | B01L 3/502715 250/371 |
| 2010/0243448 A1 | 9/2010 | Maurer et al. | |
| 2013/0244257 A1 | 9/2013 | Graeber et al. | |
| 2013/0337493 A1* | 12/2013 | Hansteen | G01N 30/88 435/34 |
| 2018/0275058 A1* | 9/2018 | Stern | G01N 21/645 |

OTHER PUBLICATIONS

Beckman Coulter, User's Guide: PA 800 plus Pharmaceutical Analysis System: System Overview (2014) (Year: 2014).*
PCT International Preliminary Report on Patentability (Chapter 1 of the Patent Cooperation Treaty) for PCT/JS2017/061611, Applicant: The Regents of the University of California, Form PCT/IB/326 and 373, dated Aug. 1, 2019 (10pages).
PCT International Search Report for PCT/US2017/061611, Applicant: The Regents of the University of California, Form PCT/ISA/210 and 220, dated Feb. 2, 2018 (4pages).
PCT Written Opinion of the International Search Authority for PCT/US2017/061611, Applicant: The Regents of the University of California, Form PCT/ISA/237, dated Feb. 2, 2018 (8pages).
Unger, Marc A. et al., Monolithic Microfabricated Valves and Pumps by Multilayer Soft Lithography, Science 288, 113 (2000); DOI: 10.1126/science.288.5463.113.
Cheung, Shilin et al., The separation and detection of PET tracers via capillary electrophoresis for chemical identity and purity analysis, Journal of Pharmaceutical and Biomedical Analysis 94 (2014) 12-18.
Dooraghi, AA et al., Betabox: a beta particle imaging system based on a position sensitive avalance photodiode, Phys Med Biol. Jun. 7, 2013; 58(11): 3739-3753, doi:10.1088/0031-9155/58/11/3739.
The extended European search report dated Nov. 29, 2019 in European Patent Application No. 17870716.2, (12 pages).
Communication pursuant to Rules 70(2) and 70a(2) EPC dated Dec. 17, 2019 in European Patent Application No. 17870716.2 (1 page).
Response to Extended European Search Report and Written Opinion dated Apr. 23, 2021 in the European patent application 17870716.2, (9pages).
Response to extended European search report dated Apr. 23, 2020 in European Patent Application No. 17870716.2, (11 pages).
Communication pursuant to Article 94(3) EPC (first Examination Report) dated May 2, 2022 in European Patent Application No. 17870716.2, (4 pages).
User's Guide, PA 800 plus Pharmaceutical Analysis System, Methods Development, PN A51965AE (Jan. 2014), Beckman Coulter, Inc., (170 pages).
Response to Communication pursuant to Article 94(3) EPC (first Examination Report) dated Aug. 25, 2022 in European Patent Applicaiton No. 17870716.2, (67 pages).

* cited by examiner

MICROSCALE DEVICE AND METHOD FOR PURIFICATION OF RADIOPHARMACEUTICALS

RELATED APPLICATION

This Application is a U.S. National Stage filing under 35 U.S.C. § 371 of International Application No. PCT/US2017/061611, filed Nov. 14, 2017, which claims priority to U.S. Provisional Patent Application No. 62/423,963 filed on Nov. 18, 2016, which are hereby incorporated by reference. Priority is claimed pursuant to 35 U.S.C. §§ 119, 371 and any other applicable statute

STATEMENT REGARDING FEDERALLY SPONSORED RESEARCH AND DEVELOPMENT

This invention was made with government support under AG049918, awarded by the National Institutes of Health and DE-SC0001249, awarded by the U.S. Department of Energy. The government has certain rights in the invention.

TECHNICAL FIELD

The technical field generally relates to devices and methods that are used in the concentration, purification, and formulation of radiopharmaceuticals.

BACKGROUND

Positron emission tomography (PET) is a real-time, in vivo 3D imaging technique that has unparalleled specificity and sensitivity for visualizing biochemical processes. Though several tracers have been advanced to the clinic, the development and translation of others is hindered by the limited availability and high production cost of these short-lived compounds. It is believed that microfluidic radiochemistry can remove this bottleneck, enabling low-cost PET tracer production on demand.

While significant development of microfluidic tools for many parts of the PET tracer production process has occurred in the last few years, there has been relatively little development of devices and methods that are used in microscale purification. One promising technology for the purification of radiotracer compounds is the use of preparative capillary electrophoresis (CE). CE is a chemical separation technique that relies on an electric field to drive a sample through a capillary or a microchannel. The separation of charged species is based on their respective interactions with the applied electric field. CE is employed in diverse applications including DNA and protein separation, detection of disease biomarkers and pharmaceutical analysis. Cheung et al. discloses that CE can be used as a replacement for HPLC to quantify impurities in batches of short-lived radioactive tracers for medical imaging via positron emission tomography (PET). See S. Cheung, J. Ly, M. Lazari, S. Sadeghi, P. Y. Keng, and R. M. van Dam, "The separation and detection of PET tracers via capillary electrophoresis for chemical identity and purity analysis," *J. Pharm. Biomed. Anal.*, vol. 94, pp. 12-18, June 2014. Despite widespread use of CE as an analytical tool, the application of CE as a preparative method is not common due to very limited sample volume. Generally, it is desirable that the injected sample not exceed ~2% of the volume of the separation channel. CE on the analytical scale typically involves analyzing samples from ~5 to 50 nL for microchips and capillaries. For PET tracer synthesis, one type of microscale synthesis device is known as electrowetting-on-dielectric (EWOD). Though the reaction volume is much smaller than conventional methods, the final crude reaction product (that needs to be purified) generated from an EWOD devices is still typically at least ~1 µL in volume. Thus, it is necessary to reconcile this at least ~20-200× volume difference in order to use CE for purification.

SUMMARY

In one embodiment, a CE-based microfluidic purification system is disclosed that enables the purification of the relatively large volumes of liquid that contain the crude reaction product. The CE-based microfluidic system may be integrated into multiple microfluidic chips (i.e., one for injection and another for detection and formulation) or, alternatively, into a single microfluidic chip. Another object of the CE-based microfluidic purification system is to incorporate a method of measuring radioactivity of the sample. Radiation detection may be linked to fraction collection so that the desired product peak can be captured from the crude reaction mixture. Another object of the CE-based microfluidic purification system is to incorporate a method of measuring or identifying non-radioactive compounds or molecules present in the sample. These non-radioactive fractions represent unwanted impurities and side-products and can be diverted to waste.

In one aspect of the invention, the volume disparity discussed above is addressed by scale-up of the capacity of the CE-based purification system. Scaling up the injection volume is made possible by scaling up the effective diameter (or width/height dimensions) and/or length of the injection plug, or by running several small-scale separations in series or parallel. According to fundamental principles of CE, scaling up the length of the injection plug would require a proportional increase in the length of the separation channel to maintain similar separation performance. This would require a longer separation time (resulting in more radioactivity decay) and is thus undesired. This would also involve operation at higher separation voltage to maintain the same separation field (which can become impractical). In contrast, scaling up the diameter or the width/height dimensions of the injected plug of fluid containing the crude product would increase the volume but is expected to achieve similar separation performance for the same capillary length. Furthermore, the volume increases in magnitude that is proportional the square of the diameter (or effective diameter in the case of non-circular fluid plugs). Accordingly, increasing the diameter by 2× would allow 4× more sample to be loaded while retaining the same injection plug length, and thus similar separation performance.

In one embodiment of the invention, CE-based purification system includes multiple microfluidic chips that work together. In this embodiment, one chip is used as an injection chip while the other chip is used as a detection chip with an integrated fraction collector. A capillary, which is used for separation, is connected at one end to the microfluidic injection chip and at the other end to the microfluidic detection chip. In this hybrid design, the larger bore capillary is used for separation, while detection and product collection or isolation occurs in the downstream microfluidic detection chip. The system is able to purify relatively large crude sample volumes of at least 1 µL.

In another embodiment of the invention, CE-based purification is integrated into a single microfluidic chip. This microfluidic chip incorporates microfluidic injection of the crude product, separation or purification, and detection and fractionation of the desired product(s) in a single microfluidic chip.

In another embodiment of the invention, the microfluidic detection chip (or the single microfluidic chip incorporating injection, purification, and detection functionality) includes the ability to detect the presence of chemical and/or radiochemical species and then collect the desired species to enable the collection of the purified fraction(s) of interest. For example, optical absorbance (UV detection) may be used to detect non-radioactive impurities, although other detection modalities may also be used (e.g., using pulsed amperometric detection, capacitively-coupled contactless conductivity detection). Optionally, an extended optical path may be incorporated into the microfluidic chip design to enhance the optical absorbance signal to achieve high sensitivity and improved limit of detection. The path length for radiation detection may also be increased by using a serpentine-shaped channel in the radiation detection region to increase sensitivity in some embodiments. For radiation detection, a solid state radiation detector may be used in one embodiment. Solid state detectors are well-suited for the detection of PET tracers. By direct detection of positrons, good spatial resolution (i.e., good resolution between one peak and the next) can be achieved without the need for having shielding or collimators, as the range of positrons from, for example, fluorine-18 is very limited (e.g. ~1-2 mm in materials with density of water). For example, a radiation detector with avalanche photodiodes (APDs) or silicon photomultipliers (SiPMs) can achieve a high degree of sensitivity (e.g., greater than 80% after solid-angle correction) to positrons, and by placing the radiation detector close to the sample (e.g., in some embodiments within 100 µm of the sample). In addition, the radiation detector will capture approximately 50% of all potential decays within the detection volume (the other half being lost through the side of the device not containing the radiation detector).

In another aspect of the invention, the microfluidic detection chip (or the single microfluidic chip incorporating injection, purification, and detection functionality) includes a microscale fraction collector that is integrated therein. For example, the fraction collector can be integrated at the output of the separation chip to enable retrieval of particular peak(s) of interest observed by one or more detectors (either non-radioactive or radioactive). The fraction collector could also be integrated with a single microfluidic detection chip. Upon triggering (e.g., when a human or a computer automatically determines that the most recently detected peak corresponds to the desired one to be collected), valves present in the microfluidic chip will divert the flow from the separation region through a fluid pathway (e.g., channel) to that can be used to collect the fraction of interest. Once the peak has been completely collected, the valves will be set back to their original states so the remaining species go to the waste well. The desired purified sample is now contained in a channel segment, trapped between closed valves. Additional valves and pathways on chip can provide a means to collect this purified fraction from the chip.

This miniaturized platform provides a number of advantages. A significant advantage is the ability to miniaturize CE-based purification into a microfluidic chip measuring inches or smaller on each side, minimizing the amount of radiation shielding that is required. Measurement of positrons within a microfluidic environment allows for very high sensitivity to sample PET radioisotopes, while also retaining useful temporal resolution. This also reduces costs usually associated with radiation detection, as the shielding is drastically reduced by the smaller size of the chip platform. An ultra-compact method for tracer purification is needed for a self-shielded benchtop synthesis system that doesn't rely on being operated with a hot cell.

The platform offers versatility for numerous radiopharmaceuticals and applications. For example, multiple types of radioisotopes could be used by changing detector type, while other aspects and methods will remain the same, allowing for multitudes of applications. In the example geometry described above, the addition of the detector requires no additional resources or special techniques for fabrication, and can be easily swapped with other detection types for other radioisotopes. Microchip CE is capable of separating large biomolecules (e.g., nucleic acids and proteins), peptides, inorganic ions and chiral molecules simply by tuning separation conditions. In fact, the versatility and separation power of CE have been noted to be equal to or better than that of the HPLC in some applications. CE can successfully separate the tracers 3'-deoxy-3'-[$^{18}$F]fluorothymidine ([$^{18}$F]FLT) and 1-(2'-deoxy-2'-[$^{18}$F]fluoro-β-D-arabinofuranosyl) cytosine ([$^{18}$F]FAC) from their impurities for quality control testing purposes suggesting that it is possible to develop separation conditions for multiple different radiopharmaceuticals suitable for separating the radiopharmaceutical from impurities.

Another benefit is that the system described herein eliminates the high pressure HPLC pump (shrinking and simplifying the interface to other subsystems), and uses only small volumes of biocompatible mobile phase (simplifying the formulation process to make tracers ready for injection). The system is also accommodative to process automation so that the entire purification step will be automated to minimize the user's radiation exposure and to ensure repeatability of the purification process.

In one embodiment, a device for the purification of a radiochemical compound includes a microfluidic injection chip comprising an injection channel having at outlet at one end and a well or reservoir at an opposing end, the injection channel being configured to receive a volume of unpurified sample containing the radiochemical compound. A capillary is connected at a first end to the output of the microfluidic injection chip and is connected at another end to a microfluidic detector chip, the microfluidic detector chip having a fraction collection channel coupled at one end to the second end of the capillary and fluidically coupled at another end to a waste well or reservoir and one or more branch fraction channels intersecting with the fraction collection channel, wherein a portion of the fraction collection channel defines an optical detection region, a radiation detection region containing a radiation detector, wherein a plurality of valves are positioned along the branch fraction channels and along the fraction collection channel. The device or system includes a high voltage power supply having a first conductor in contact with the well or reservoir of the microfluidic injection chip and a second conductor in contact with the waste well or reservoir of the microfluidic detector chip.

In another embodiment, a device for the purification of a radiochemical compound includes a microfluidic injection chip that has an injection channel having at outlet at one end and a well or reservoir at an opposing end and a plurality of intersecting microfluidic branch channels, wherein a plurality of microfluidic valves are positioned along the intersecting branch channels and along the injection channel. The valves are positioned along the injection channel and define an injection volume, and wherein one of the branch channels is configured to receive a volume of unpurified sample containing the radiochemical compound. A capillary is connected at a first end to the output of the microfluidic injection chip. A microfluidic detector chip is connected to a second end of the capillary, the microfluidic detector chip having a fraction collection channel coupled at one end to the second end of the capillary and fluidically coupled at another end to a waste well or reservoir and one or more branch fraction channels intersecting with the fraction collection channel, wherein a portion of the fraction collection channel defines an optical detection region containing one or more optical waveguides, a radiation detection region containing a radiation detector, wherein a plurality of valves are positioned along the branch fraction channels and along the fraction collection channel. The device or system includes a high voltage power supply having a first conductor in contact with the well or reservoir of the microfluidic injection chip and a second conductor in contact with the waste well or reservoir of the microfluidic detector chip.

In another embodiment, microfluidic chip device for the purification of a radiochemical compound includes a microfluidic chip substrate. The microfluidic chip substrate includes an injection channel having a buffer well or reservoir at one end thereof, the injection channel being configured to receive a volume of unpurified sample containing the radiochemical compound. The microfluidic chip substrate further includes a purification region comprising a serpentine separation channel segment and coupled at an upstream end thereof to an output of the injection channel. A fraction collection channel is coupled to a downstream end of the serpentine separation channel segment at one end and at another end to a waste well or reservoir and one or more branch fraction channels intersecting with the fraction collection channel, wherein a portion of the fraction collection channel defines an optical detection region, a radiation detection region containing a radiation detector, wherein a plurality of valves are positioned along the branch fraction channels and along the fraction collection channel. The device or system includes a high voltage power supply having a first conductor in contact with the buffer well or reservoir and a second conductor in contact with the waste well or reservoir of the microfluidic detector chip.

BRIEF DESCRIPTION OF THE DRAWINGS

In FIG. 8C, the valves along the injection channel are opened so that the sample may move down the channel.

DETAILED DESCRIPTION OF ILLUSTRATED EMBODIMENTS

Figure 1:
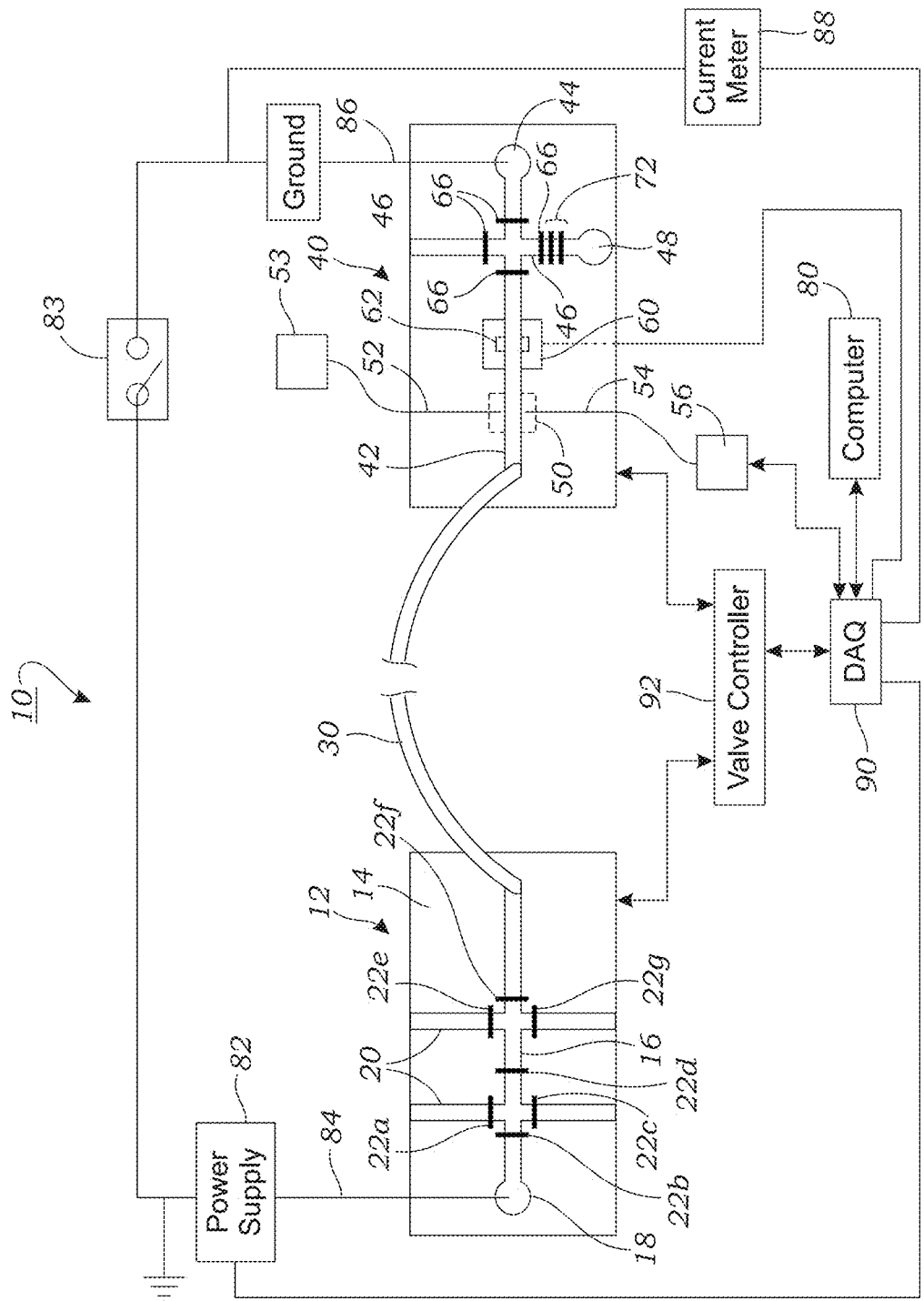
FIG. 1 illustrates one embodiment of a device or system for the purification of a radiochemical compound. This embodiment employs a microfluidic injection chip, a CE capillary, and a microfluidic detector chip.

FIG. 1 illustrates one embodiment of a device or system 10 for the purification of a radiochemical compound (e.g., radiolabeled PET tracer). The device 10 incorporates a microfluidic injection chip 12 that is formed in a substrate 14 made of, for example, a polymer such as poly(dimethylsiloxane) (PDMS), glass, or quartz. The microfluidic injection chip 12 includes a plurality of microfluidic channels formed therein that are used during the injection process to inject a volume of fluid containing the radioactive species into a downstream capillary 30. In one embodiment, the microfluidic injection chip 12 includes an injection channel 16 that is used to selectively define the volume of fluid that is to be injected into the downstream capillary 30. The dimension of the injection channel 16 may vary but typically has a width within the range of 50 µm to 500 µm, a height within the range of 50 µm to 500 µm, and length within the range of 10 mm to 300 mm. For example, in one embodiment, the width of the injection channel 16 may be around 250 µm, the height of the injection channel 16 may be around 250 µm, and the length around 16 mm. The volume of fluid contained in the injection channel 16 is, in one embodiment, around 1 µL or less. In still other embodiments, the volume of fluid can be increased (e.g., up to about 10 µL) by using a longer serpentine shaped injection channel 16, or by increasing the width and/or height of the injection channel 16. As seen in FIG. 1, one end of the injection channel 16 includes a well or reservoir 18 that is dimensioned to hold a sample containing the crude radioactive compound of interest. The volume of the well or reservoir 18 may vary but typically may contain up to about 1 µL of fluid. For radiosynthesis applications, the sample may include a crude radioactive compound containing sample that arrives from a separate microfluidic radiochemistry chip such as an electrowetting-on-dielectric (EWOD) chip (not illustrated in FIG. 1) that is used form the crude product. Typical volumes of crude product produced by small volume radiochemistry chips are at least ~1 µL in volume. Droplets from the EWOD chip may be used to fill the well or reservoir 18.

Still referring to FIG. 1, the microfluidic injection chip 12 includes a plurality of branch channels 20 that intersect with the injection channel 16. The branch channels 20 are used to load the microfluidic injection chip 12 with sample as well as buffer solution. The width and height dimensions of the branch channels 20 may be similar to those of the of the injection channel 16. For example, the branch channels 20 may have a width within the range of 50 µm to 500 µm. The length of the branch channels 20 may vary. In some embodiments, the branch channels 20 terminate at respective ports (not shown) located on the microfluidic injection chip 12. These ports may be used to load sample, buffer, or other reagents into the microfluidic injection chip 12. Various fluid pathways may be used to load sample, buffer, or other reagents into the microfluidic injection chip 12. This includes active or passive fluid pathways on a separate radiochemistry chip or it may be tubing that interfaces with the microfluidic injection chip 12.

As seen in FIGS. 1 and 2A-2D, the microfluidic injection chip 12 includes a plurality of valves 22a, 22b, 22c, 22d, 22e, 22f, 22g that are located either in the branch channel 20 or in the injection channel 16. The valves are each controllable or actuatable independently. In one embodiment, the valves 22a, 22b, 22c, 22d, 22e, 22f, 22g are pneumatically controllable valves that can selectively close to isolate branch channel 20 and/or injection channel 16 (or portions thereof) using a membrane or flexible substrate that can expand/retract in response to applied pneumatic pressure to close off (or open) microfluidic channels or junctions. FIG. 3 schematically illustrates one such valve 22b. The valve 22b is formed at the intersection between a fluid-containing channel such as injection channel 16 or branch channel 20 and a control channel 24 that carries a pressurized source of gas. As seen in valve open configuration of FIG. 3, the injection channel 16 (in this example) is in the open state; allowing the passage of fluid along the length of the injection channel 16. In the open state, the control channel 24 is not pressurized. In contrast, the closed configuration of FIG. 3 illustrates pressure (p) in the form of a pressurized gas being applied to the control channel which expands and compresses the injection channel 16 into a closed state such that fluid cannot pass the valve 22b. The control channel 24 is connected to a source of pressurized gas (not shown) which may be connected to the microfluidic injection chip 12 via off-chip manifolds or valves which can be used to selectively pressurized the various control channels 24. Examples of such valves may be found in International Patent Application Publication No. WO 2002-043615 and Unger et al., Monolithic Microfabricated Valves and Pumps by Multi-layer Soft Lithography, Science, Vol. 288, No. 7, pp. 113-116 (2000), which are incorporated herein by reference. Such valves 22b may be formed in a polymer layer 25a such as PDMS which is bonded to a rigid substrate 25b such as glass or the like.

Figure 2A:
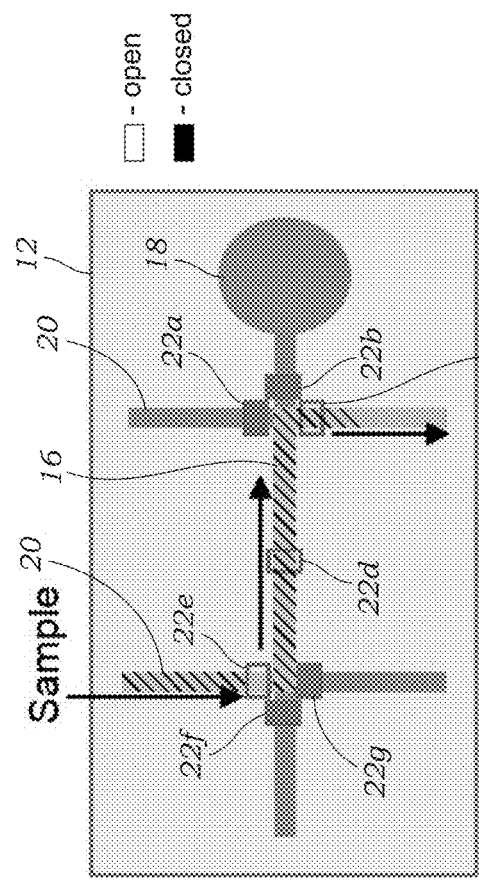
FIG. 2A illustrates a process of filling or loading the microfluidic injection chip with a buffer solution.
Figure 2B:
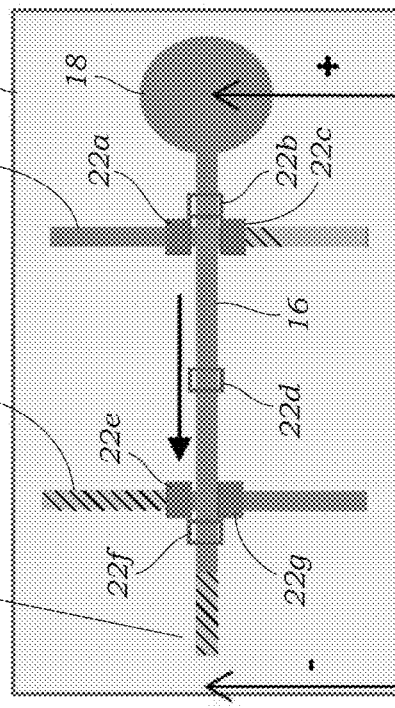
FIG. 2B illustrates a process of loading a sample containing crude, unpurified radioactive tracer in the microfluidic injection chip.
Figure 2C:
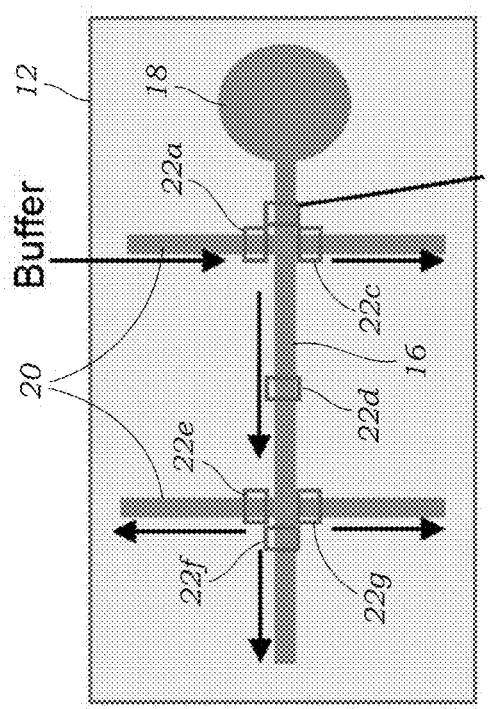
FIG. 2C illustrates the closing of both valves in the injection channel of the microfluidic injection to define the fixed volume or plug of crude sample that is to be run through the CE capillary.
Figure 2D:
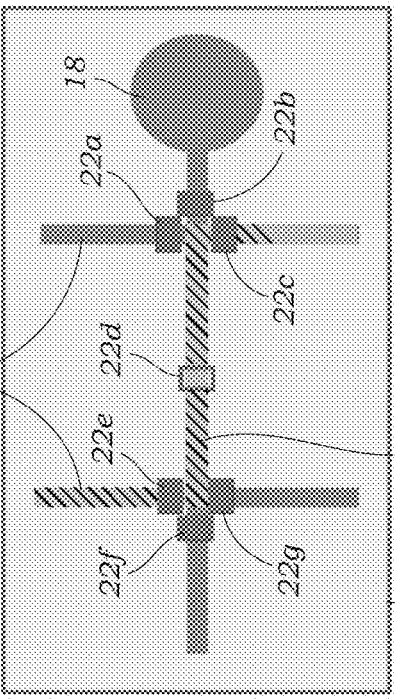
FIG. 2D illustrates the opening of both valves in the injection channel of the microfluidic injection and the application of the high voltage to perform the CE separation process.
Figure 3:
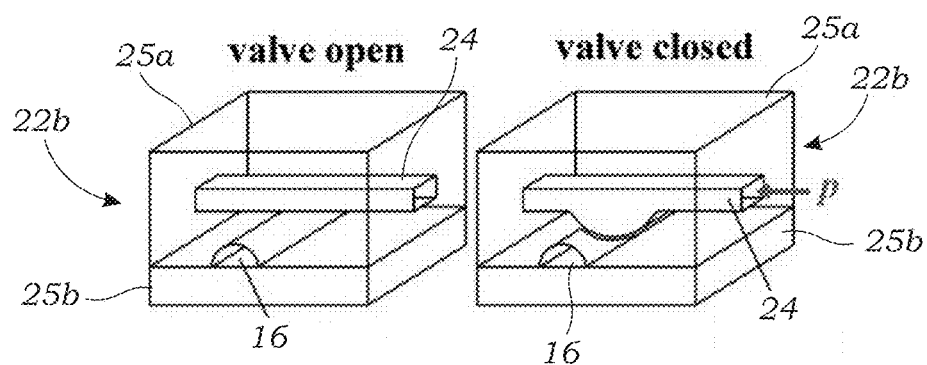
FIG. 3 schematically illustrates a pneumatically controllable valve that can selectively close to isolate a microfluidic channel using a membrane or flexible substrate that can expand/retract in response to applied pneumatic pressure to close off (or open) microfluidic channels or junctions. The valve is illustrated in the open state (left) and the closed state (right).

With reference to FIGS. 2A-2D, a sequence of operations of the valves 22a, 22b, 22c, 22d, 22e, 22f, 22g is illustrated for first priming the microfluidic injection chip 12 with a buffer solution (FIG. 2A), followed by loading of the sample (FIGS. 2B and 2C), and injection (FIG. 2D). With reference to FIG. 2A, a buffer solution is loaded into the device via one of the branch channels 20. In this operation, all valves 22a, 22b, 22c, 22d, 22e, 22f, 22g are in the open state. The buffer solution may include a salt solution such as phosphate buffered saline (PBS) mixed with a surfactant such as Sodium Dodecyl Sulfate (SDS) anionic surfactant. For example, 30 mM PBS mixed 100 mM SDS is one buffer solution that may be used for separation. With reference to FIG. 2B, valves 22a, 22b, 22f, and 22g are closed and fluid containing the sample is then loaded into one of the other branch channels 20 to fill the injection channel 16 (arrows indicating direction of flow). Loading of the sample into the microfluidic injection chip 12 may occur through off-chip application of pressure to push fluid into the microfluidic injection chip 12 or vacuum to pull fluid into the microfluidic injection chip 12. Alternatively, various on-chip pumps (not illustrated in FIGS. 2A-2D) may be used to pump the sample into the injection channel 16. Off-chip or external pumps may also be used to load the sample with the injection channel 16. Electrokinetic injection may also be employed to load the injection channel 16 with crude sample. In such embodiments, the valves 22a, 22b, 22c, 22e, 22f, 22g may be omitted entirely. In addition, the volume of crude sample that is loaded into the injection channel 16 may not be fixed. Referring back to FIG. 1, once the sample that contains the radioactive crude product has been loaded into the injection channel, valves 22a, 22b, 22c, 22e, 22f, 22g are closed as illustrated in FIG. 2C. Once the sample has been loaded into the injection channel 16, valves 22b and 22f are opened and a high voltage (direct current) is applied to move the plug of sample loaded into the injection channel 16 down the injection channel to the outlet 24 of the microfluidic injection chip 12 and into the capillary 30.

It should be noted that additional valves 22 and branch channels 20 may be added along the length of the injection channel 16 to be able to provide varying volumes available to be injected from the microfluidic injection chip 12. For example, valve 22d along with a branch channel connected thereto (not illustrated) could be used to make a smaller plug of fluid that is injected. Various valves 22 and branch channels positioned along the length of the injection channel 16 can provide user with the ability to load variable and large volumes into the microfluidic injection chip 12. While the injection channel 16 illustrated in FIGS. 2A-2D is illustrated as being linear it should be appreciated that different shapes may be employed. For example a serpentine injection channel 16 could provide added length while still being able to be accommodated on the small size of the microfluidic injection chip 12. An example one type of volumetric microfluidic injection chip 12 includes those disclosed in International Patent Application No. PCT/US2017/55607 entitled Volumetric Micro-Injector for Capillary Electrophoresis, which is incorporated by reference herein.

Referring back to FIG. 1, a wide-bore capillary 30 is connected to the output of the microfluidic injection chip 12. The diameter of the capillary may vary but typical commercial wide-bore capillaries having IDs of greater than 100 μm and up to about 1 mm may be used. In one preferred embodiment, the internal diameter of the capillary 30 is coated with silica. In other embodiments, the internal diameter or lumen of the capillary 30 may be packed with a porous material in aid in separation. The length of the capillary 30 may vary depending on the ID of the capillary 30. Using a 21 cm capillary length, the expected sample capacities are 0.11 μL (ID of 180 μm) and 0.93 μL (ID of 530 μm), respectively. For a 50 cm long capillary, the capacities are 0.25 (ID of 180 μm) or 2.2 μL (ID of 530 μm), respectively. As a general rule, the capillary 30 (or separation channel 112 discussed below) should have a volume that is about 100× or more than the volume of the sample; although at smaller IDs this would make the nominal length of the capillary 30 very long (e.g., several meters in length). Preliminary experiments were performed at a field of 200 V/cm, which requires a potential of ~4 or 10 kV for these capillary lengths. Since it is not very practical to work with higher voltages, and because reducing the voltage adversely impacts performance (i.e., longer separation time, increased diffusive band broadening), 50 cm is generally set as an upper bound on the length of the capillary 30 at these dimensions.

As seen in FIG. 1, the opposing end of the capillary 30 interfaces with a downstream microfluidic detector chip 40. The microfluidic detector 40 chip includes a fraction collection channel 42 that interfaces with or is otherwise fluidically coupled to one end to the end of the capillary 30. The fraction collection channel 42 is fluidically coupled at an opposing end to a waste well or reservoir 44 and one or more branch fraction channels 46 intersecting with the fraction collection channel 42. One of the branch fraction channels 46 may be used to divert the purified product to a collection well or reservoir 48. The microfluidic detector chip 40 includes detector functionality for detecting separated species that exit the capillary 30. In one embodiment, the microfluidic detector chip 40 includes an optical detection region 50 along a portion of the fraction collection channel 42 that is optically interrogated by an optical sensor. The optical detection region 50, in one embodiment, includes at least one illuminating waveguide 52 that transmits light (e.g., ultra violet light) along or across the fraction collection channel 42. The illuminating waveguide 52 may be connected using a source of UV light 53 such as a Deuterium lamp. Transmitted light that passes through the fluid contained in the fraction collection channel 42 is collected by at least one detecting waveguide 54 that transmits the received light to a detector 56 such as a spectrophotometer. In one embodiment, the waveguides 52 include optical fibers (e.g., 125 μm diameter fibers) that are placed in receiving channels contained in the microfluidic detector chip 40. The waveguides 52, 54 may be held in their respective receiving channels using a friction fit or, alternatively, an adhesive may be added to secure the waveguides 52, 54 in the microfluidic detector chip 40. The regions of the fraction collection channel 42 that receive the waveguides 52, 54 preferably have a flat channel interface where the light enters/exits the fraction collection channel 42. Typically, the bottom channels of the microfluidic detector chip 40 are rounded (so that elastomeric valves can close completely) such as that illustrated in FIG. 3. The formation of flat interfaces can be accomplished in the manufacturing process using two types of photoresist. One type retains the square shaped side walls while the other can be melted/reflowed to give the rounded shape. In yet another alternative, the waveguides 52, 54 are formed using a liquid or even air. The edge of the microfluidic detector chip 40 can be connected to optical fibers and other off-chip components. In still another embodiment, the waveguides 52, 54 may be omitted entirely and an off-chip, out-of-plane detector could be used to optically interrogate the fraction collection channel 42. For example, the fraction collection channel 42 can be optically interrogated by a detector that is positioned on the top (or bottom) of the microfluidic detector chip 40.

Figure 4:
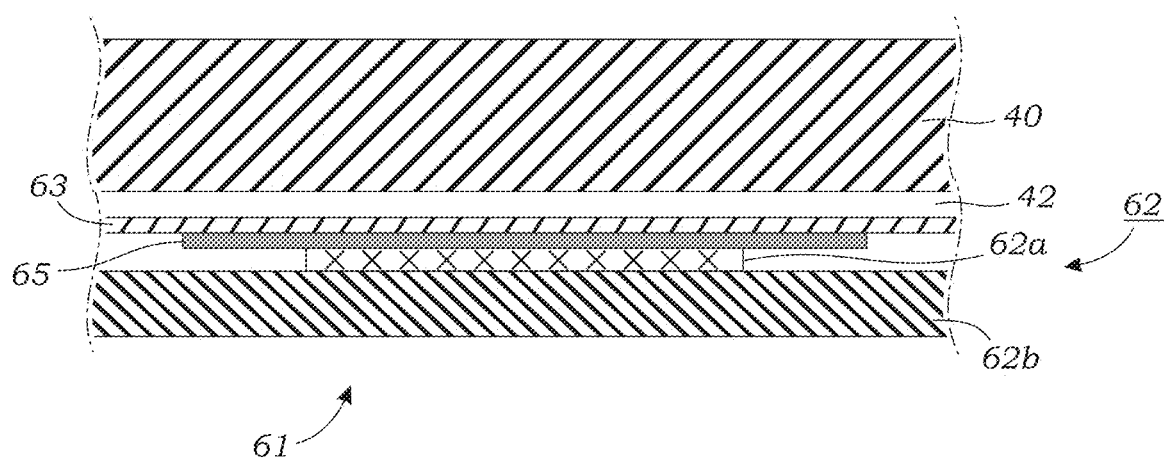
FIG. 4 illustrates a cross-sectional view of the radiation detector mounted in the microfluidic detector chip.

The microfluidic detector chip 40 further includes a radiation detection region 60 located along a portion of the fraction collection channel 42 and is used to detect radiation of chemical species contained in the fluid. The radiation detection region 60 includes a radiation detector 62, as seen in FIGS. 1, and 4, that is positioned adjacent to the fraction collection channel 42. In one preferred configuration, the radiation detector 62 is located within recess or cutout 61 such that the active surface of the radiation detector 62 can sit flush against a thin layer 63 of PDMS (e.g., 100 μm) that separates the radiation detector 62 from the fraction collection channel 42. For example, typical photolithographic techniques may be used to make a PDMS microfluidic detector chip 40. SU-8 is patterned on a silicon wafer to form a negative mold for the chip design. Liquid PDMS is then poured over this pattern and cured at 80° C. The cured chip was removed and holes punched for the inlet for the capillary 30 and a buffer waste well or reservoir 44 (where negative electrode is placed in CE setup). Holes may also be punched for the collection well or reservoir 48. In an alternative configuration, the waste well or reservoir 44 and/or the collection well or reservoir 48 may instead be located off-chip, connected by capillary tubing.

Instead of bonding the PDMS structure to a single glass or PDMS substrate as is done with a conventional two layer design, in one preferred embodiment of manufacturing the microfluidic detector chip 40, the PDMS is first bonded to a ~100 μm thick layer 63 of cured PDMS via corona discharge treatment. This "thin" layer may be made of a different material (e.g., polymer sheets, mylar, glass, or even metal sheets) and may have a thickness that is less than 100 μm provided the structure still maintains sufficient structural integrity. An additional, thick (several mm) layer of PDMS is then bonded below this 100 μm layer to provide additional mechanical stability. Valves 66 may be formed in a thick, top layer that contains the microvalve actuation channels in the bottom surface (as seen in FIG. 3) that is bonded to the PDMS structure that contains the microfluidic features of the microfluidic detector chip 40. In the radiation detection region 60 of this thicker layer, there is a cutout or recess 61 such that the active surface of the radiation detector 62 can sit flush against the bottom of the thin PDMS layer 63 (i.e., 100 μm below the fraction collection channel 42). This is important for direct detection of beta particles (e.g., positrons, electrons) emitted during radioisotope decay, to minimize the attenuation, and to maximize the solid-angle in the source-to-detector configuration. This cutout feature also has a secondary benefit of ensuring that all fabricated chips 40 will sit in the same position with regard to the same detector 62, increasing repeatability, though alignment may also be enhanced by adding alignment features elsewhere to both the chip 40 and the detector 62 and associated electronic circuitry. While all three layers are made of PDMS, other elastomers or materials such as perfluoropolyether (PFPE), fluorosilicone, FFKM (Kalrez, Chemraz), SIFEL, and the like may be used.

FIG. 4 illustrates a side view of the detector 62 mounted adjacent to the thin layer 63 of PDMS in the cutout or recess 61. The thickness of the thin layer is less than about 500 μm, for example, 100 μm. The detector 62 includes a detector surface 62*a* that bonded or adhered to the thin layer 63 of PDMS using a passivation layer 65. The detector 62 includes a ceramic backing 62*b*.

In one embodiment, the detector 62 is an avalanche photodiode (APD) (Radiation Monitoring Devices Incorporated) that has a 2 mm×2 mm active area. The detector 62 is mounted on a ceramic substrate. The detector 62 was modified so that the electrical terminals for the bias power supply were altered to ensure that the APD itself was the "tallest" feature on the ceramic substrate. In order to protect the device against unwanted optical photons from the surrounding equipment, a passivation layer was added consisting of a 1 μm layer of parylene C, followed by a 200 nm layer of gold, and another 1 μm layer of parylene C. The 200 nm thickness was chosen by empirical testing to be a thickness that seem to block all light.

The detector 62 is biased at 1750V using a high-voltage power supply. Electrical filtering is placed on the supply before the detector 62 to stabilize the power and remove any fluctuations. The device 62 generates an electrical output in response to incident radiation. The output current first passes through a transimpedance amplifier as described in Dooraghi et al. Physics in Biology and Medicine 58: 3739, 2013, which is incorporated by reference herein. This amplified signal is then routed through a shaping amplification step, consisting of a high- and low-pass filter in series to ensure detected positrons have pulse characteristics (~50 ns). Peaks are compared against a static threshold to remove electronic noise, and then fed as digital pulses to a counting device and DAQ (e.g., DAQ 90) to determine the amount of radiation (counts per sec).

To minimize the size of the overall size of the microfluidic detector chip 40, in one embodiment, utilizes a solid-state radiation detector 62; in particular an avalanche photodiode (APD), which has very high efficiency of detecting positrons. Due to the small thickness of the APD detector 62, and the relatively low density of silicon, the cross-section of gamma ray interactions is very small and the device is sensitive primarily to direct positron interactions. Given the short range of positrons (~1 mm average in water for positrons from F-18), an important design decision is keeping the radiation detector 62 as close to the activity as possible. Keeping the detector 62 close also maximizes the solid-angle, ensuring that close to half of all emitted positrons in the detection region can hit the detector 62 (the other half are directed away from the detector).

The surface of the APD detector 62 is not chemically-resistant, however, and combined with the high bias voltage applied to the detector 62 for usage, there must be electrically and chemically insulating material between the detector and the liquid. The detection is performed near the ground end of the capillary electrophoresis circuit (explained in more detail below) so the potential within the fraction collection channel 42 is relatively low. Similarly, the side of the silicon APD detector 62 in closest proximity to the sample is near ground potential. Breakdown through the thin layer 63 of PDMS is not an issue because the breakdown strength of PDMS at 100 μm thickness is 1000V, well above the expected ~400V present in the fraction collection channel 42 (assuming detector 62 is ~2 cm upstream of the waste well (electrical ground), separation length is ~60 cm and separation voltage is ~12 kV).

Another important design factor is the size of the radiation detection region 62. By detecting positrons, the detector 62 is sensitive only to the sample directly above the detector 62 and not sample more distantly located in the fraction collection channel 42 on its way into the radiation detection region 60 (or leaving the radiation detection region 60). This helps to ensure good temporal resolution as the sample moves over the detector 62, which in turns enables good separation resolution of peaks after CE separation. Furthermore, the use of a physically small (area) detector 62 helps to improve temporal resolution in the moving sample, i.e. it is only sensitive to a short segment of liquid, but as a result less radiation is detected at any given time. A larger detector 62 will have the opposite effects. Based on modeling done with the solid state APD detector 62, the detector 62 is very sensitive to liquid within ~1 mm depth of the detector 62, and very insensitive to sample that is outside the boundaries of the detector 62. This low sensitivity to distant radiation sources helps to ensure that other sources (e.g. the waste well or chamber 44, the capillary 30 connected to the chip 40) where high activity may be found, will not interfere with the detected signal.

Another important design criterion is maximizing the sensitivity of the detector 62. Because the detector area is small, and the sample will pass quickly into and out of the radiation detection region 60, a relatively low number of decay events may be available for detection. For example, a sample of FLT moved at a linear speed of ~1 mm/s, meaning the sample is only in the detection region for 2 seconds. This is one of the reasons for choosing the APD detector 62; it has very high efficiency of detection such that nearly all available positrons will be detected to maximize signal to noise. High sensitivity also opens up the possibility to run faster separations (e.g., by increasing the separation field), which would reduce radioactive decay of the product being purified.

Figure 5:
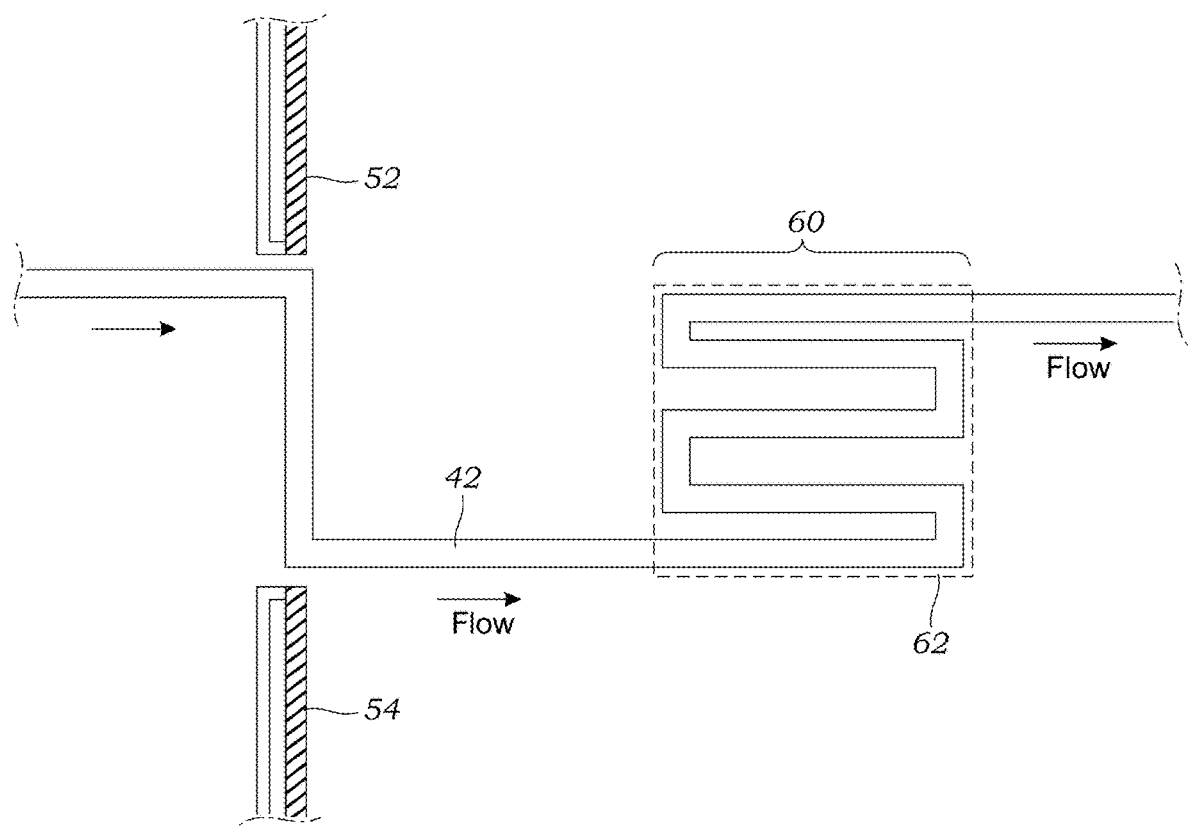
FIG. 5 illustrates the layout of the detection portion of the fraction collection channel in the microfluidic detector chip according to one embodiment.

To increase the signal, one can also increase the length of the fraction collection channel 42 that passes over the detection region 60, e.g. by using a serpentine channel design. FIG. 5 illustrates one embodiment that employs a serpentine-shaped fraction collection channel 42 that is used in the region adjacent to the radiation detector 62. FIG. 5 illustrates a five (5) pass embodiment that increases the path length 5× with respect to a straight configuration. Of course, different numbers of serpentine turns can produce different pass configurations (e.g., three pass, seven pass, etc.). Although the signal is increased, this is achieved at the expense of reduced spatial resolution as the sample is in the detection region 60 for a longer time. Tapered turns such as those illustrated in FIG. 7B may be added to prevent the effects of dispersion so that signal peaks will be sharp after the detector. As also seen in FIG. 5, the path length of the optical detection region 50 may also be increased to increase the responsive signal obtained using the waveguides 52, 54. In this embodiment, the optical pass traverses a length or segment of the fraction collection channel 42 rather than just the width.

Figure 6:
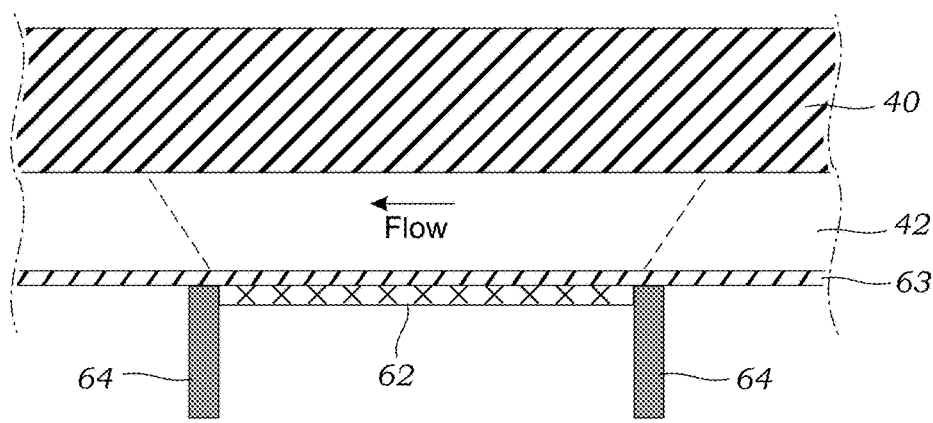
FIG. 6 illustrates a cross-sectional view of the radiation detector mounted in the microfluidic detector chip according to another embodiment that utilizes a collimator.

In one embodiment, the radiation detector 62 detects radiation emitted by the radioactive product that is contained in the fraction collection channel 42. For example, the radiation detector 62 may detect gamma radiation. This includes solid state detectors such as APDs and SiPMs but also include scintillator that generates light that is detected by a PMT or image sensor (e.g., CMOS or CCD). In such embodiments, an optional collimator 64 may be needed so that gamma radiation, which can travel longer distances than positrons or electrodes, is only detected when the radioactive product passes directly by the detecting surface radiation detector 62. FIG. 6 illustrates one embodiment of a collimator 64 that is used to limit or prevent the detector 62 from detecting gamma radiation that may be emitted from radioactive species located in other components in the device (e.g., in the capillary 30 or upstream of the detector 62). FIG. 6 illustrates dashed areas in the fraction collection channel 42 that represent potential spillover zones. The collimator 64 may be made of a metallic material (e.g., lead, tungsten, or certain steels) that are known to block or attenuate the transmission of gamma radiation. In another embodiment, the radiation detector 62 may detect positrons instead of gamma rays. For example, an avalanche photodiode (APD) detector 62 can be used to detect positrons. Positrons travel only a short distance so when an APD detector 62 is used, there is no need for a collimator 64. In another embodiment, the detector 62 may include a silicon photomultiplier (SiPM). SiPMs can be purchased commercially (SensL) in a variety of sizes (e.g., 1×1 $mm^2$ or 3×3 $mm^2$).

In another embodiment, a pair of photodiodes may be used for the radioactivity detector 62 with one photodiode placed as close as possible to the flow path (sensitive to positrons as well as gammas), and another placed below the first, sensitive only to gammas. Subtraction of the gamma signal produces a corrected readout of the concentration of positrons. By adjusting the gain, the system could operate in different ranges of radioactivity (up to the 1000 mCi levels expected here) with a dynamic range of four (4).

With the microfluidic detector chip 40 having both an optical detection region 50 and a radiation detection region 60, this enables the collection of chromatograms (i.e., electropherograms) with sufficient information to separate the radiolabeled PET tracer from non-radioactively labeled impurities. The optical detection region 50 and the radiation detection region 60 are formed during fabrication of the microfluidic detector chip 40.

The microfluidic detector chip 40 also includes the ability to fractionally collect species that are separated during the CE process. In this regard, as seen in FIG. 1, the microfluidic detector chip 40 includes one or more valves 66 that can be used to trap or shunt flow to a collection well or chamber 48 or a waste well or chamber 44. For example, the collection well or chamber 48 may be connected to the fraction collection channel 42 via a branch fraction channel 46. A pump 72 may also be incorporated into the microfluidic detector chip 40 to move the purified product to the collection well or chamber 48. Pumping action may also be provided using positive pressure or vacuum pressure applied to branch fraction channels 46. The valves 66 may be pneumatically actuated valves like those described herein in the microfluidic injection chip 12 and may be controlled automatically via the computer 80 in response to detection of non-radioactive species in the optical detection region 50 or detection of radioactive species in the radiation detection region 60. In this regard, waste products can be diverted to one area of the microfluidic detector chip 40 (e.g., waste well 44) while the desired products may be diverted or trapped on another area of the microfluidic detector chip 40 (e.g., collection chamber or well 48). For example, after being trapped or diverted, the desired products may be transferred off of the microfluidic detector chip 40 (or to an adjacent chip) for reformulation and use. In one embodiment, relatively large volumes of product may be isolated using the platform described herein. Typical final volumes may be up to several microliters of purified tracer.

As seen in FIG. 1, a high voltage (DC) power supply 82 is used to drive CE separation and may be coupled to a computer voltage relay 83 that is used to selectively energize a conductor or probe 84 that contacts with a buffer solution contained in the well or reservoir 18 of the microfluidic injection chip 12. The power supply 82 is also coupled to a ground conductor, contact, or probe 86 that is located in a well 44 of the microfluidic detector chip 40 to complete the circuit. A current meter 88 is used to measure current and interfaces with the computer 80 and data acquisition board or DAQ 90 as illustrated in FIG. 1. The power supply 82 is used to provide the electrophoretic potential and drive the fixed volume of sample into the capillary 30 for separation and detection. Typically, voltages of up to 12 kV may be applied. For separation, the voltage is applied typically for several or tens of minutes. A valve controller 92 also interfaces with the DAQ 90 and computer 80 so that the valves 22 may be actuated as explained herein for injection, separation, and detection processes. For example, the computer 80 may be programmed to trap or isolate a plug of fluid from the fraction collection channel 42 after the radiation detector 62 detects radiation. This plug of fluid which contains the desired radioactive compound or species (e.g., radiotracer) that has been separated from the crude mixture can be pumped to the collection cell or reservoir 48 by activating the pump 72.

Figure 7A:
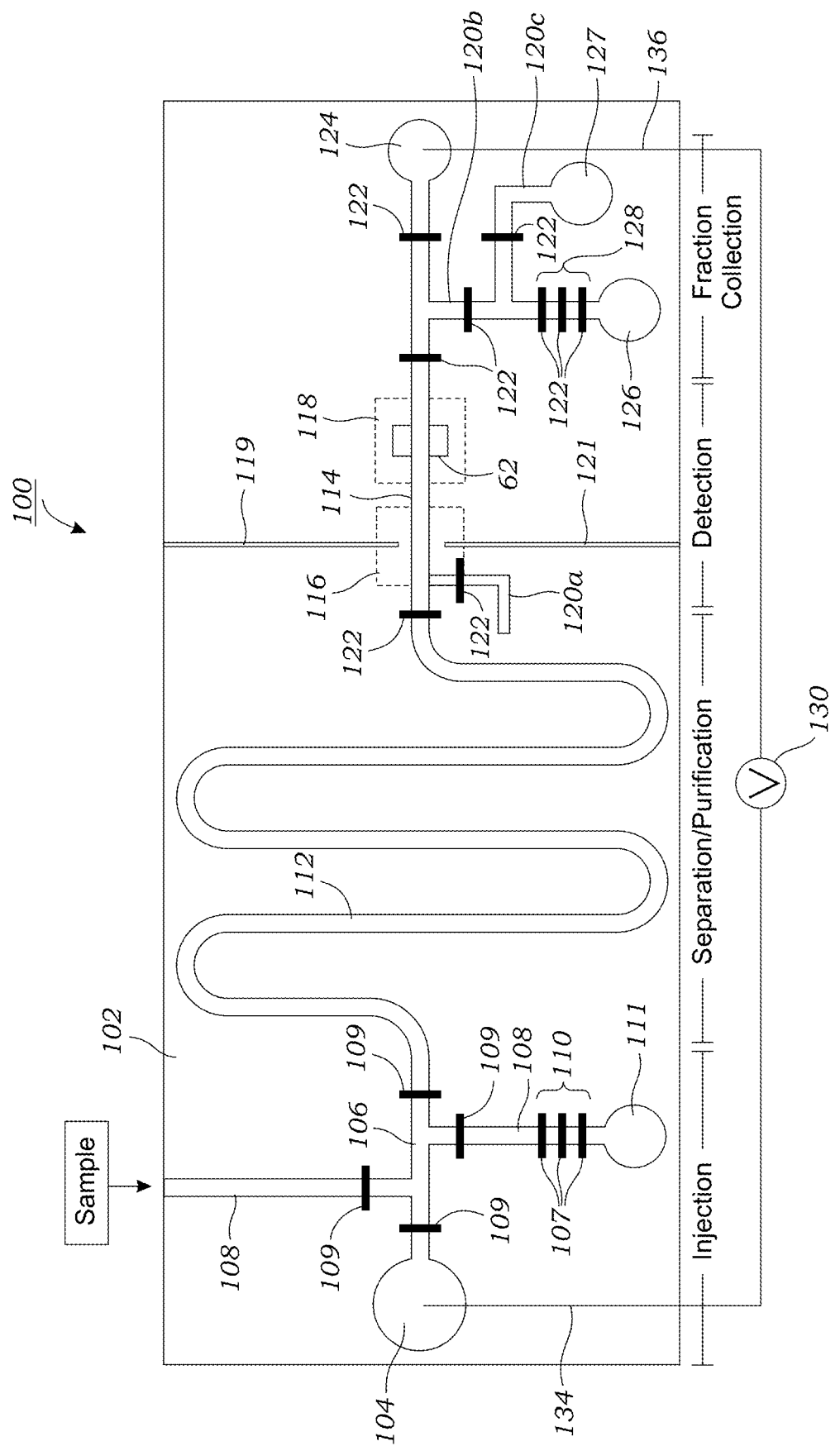
FIG. 7A illustrates another alternative embodiment that uses integrated microfluidic CE chip. A single microfluidic chip is used for injection, separation/purification, detection, and fraction collection.
Figure 12A:
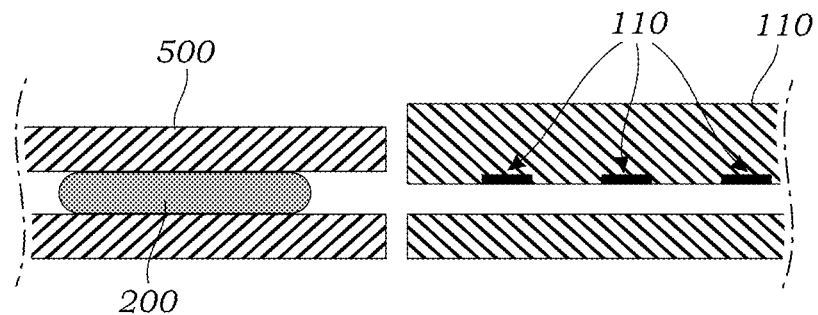
FIGS. 12A-12C illustrates a sequence of operations for the loading of a sample containing the crude radioactive tracer using a separate EWOD chip.
Figure 12B:
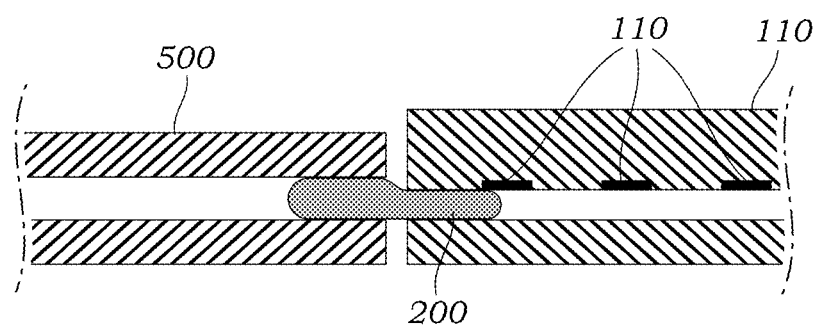
Figure 12C:
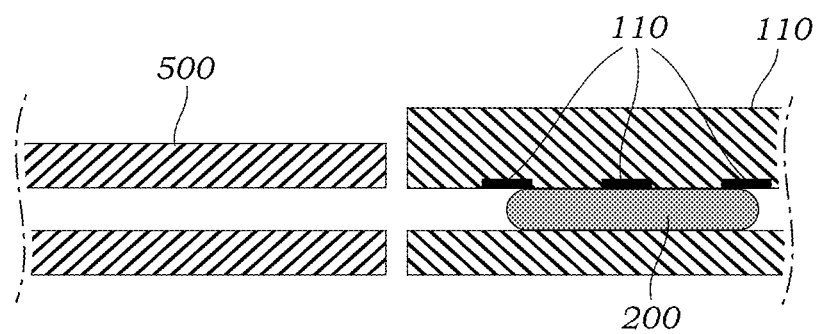

FIG. 7A illustrates another alternative embodiment where the functionality of the microfluidic injection chip 12, the capillary 30, and the microfluidic detector chip 40 of the prior embodiment are all integrated into a single, integrated microfluidic CE chip 100. In this embodiment, a sample which may be in the form of a droplet 200 or multiple droplets which may be generated in a separate EWOD chip 500 as seen in FIGS. 12A-12C, is then transferred to the integrated microfluidic CE chip 100. As seen in FIG. 7A, the integrated microfluidic CE chip 100 is formed in a substrate 102 such as that described in the prior embodiment. The integrated microfluidic CE chip 100 includes a buffer well or reservoir 104 that contains a buffer solution (e.g., PBS and surfactant solution as described herein). The buffer well or reservoir 104 is coupled to an injection channel 106 that is similar to the injection channel 16 of the prior embodiment. A plurality of branch channels 108 intersect with the injection channel 106 and are used to deliver the crude sample to the injection channel 106. The branch channels 108 may also be used to deliver buffers or other reagents to the injection channel 106.

A plurality of valves 109 are located in the injection channel 106 and the branch channels 108 and are used to load a defined volume of sample for injection in the same manner described with respect to the microfluidic injection chip 12 of FIGS. 1 and 2A-2D. The integrated microfluidic CE chip 100 may include an on-chip pump 110 that can be used to pump the crude sample that is loaded into one of the branch channels 108 into the injection channel 106. For example, a separate EWOD chip such as that illustrated in FIGS. 12A-12C, may be used to generate a droplet that contains the crude, unpurified radiotracer. The droplet is transferred to the branch channel 108 and then pumped into the injection channel 106 where it is ready for separation. The pump 110 may operate as a series of valves 107 that actuate to create peristaltic pumping action of the fluid contained in the integrated microfluidic CE chip 100. The pump 110 may lead to a waste well or reservoir 111 where pumped fluid can be retained. Alternatively, instead of an on-chip pump 110, positive pressure may be applied to push fluid into the branch channels 108 and injection channel 106. A source of vacuum could also be used to pull fluid into the branch channels 108 and the injection channel 106. In another alternative embodiment, a dedicated well or reservoir (not illustrated) formed on the integrated microfluidic CE chip 100 that connects to the injection channel 106 via a branch channel 108 may be used. Electrokinetic injection may also be used to load the injection channel 106. In these alternative embodiments, the valves 109 may be omitted entirely and the volume of fluid that contains the crude radioactive tracer compound may not have a fixed volume.

Referring back to FIG. 7A, the valves 109 are used to secure a plug of fluid that contains the crude, unpurified radioactive tracer compound. The injection channel 106 is fluidically coupled at the other end to a purification region that includes a serpentine shaped separation channel segment 112 as seen in FIG. 7A. The serpentine shaped separation channel segment 112 has a plurality of turns so that a relatively longer length of channel is created. The serpentine shaped separation channel segment 112 may have a width within the range of about 250 µm to 1,000 µm, a height within the range of about 250 µm to 1,000 µm, and a length within the range of about 100 mm to 1,600 mm. The internal surface of the serpentine shaped separation channel segment 112 may be coated with silica that is used for separation of the species contained in the crude product that is flowed along the serpentine shaped separation channel segment 112. The serpentine shaped separation channel segment 112 terminates at a downstream end at a fraction collection channel 114. The fraction collection channel 114 includes, in one embodiment, an optical detection region 116 that is used to optically interrogate the contents of the fraction collection channel 114 as well as a radiation detection region 118 that is used to detect the presence of radioactive chemical species or compounds in the fraction collection channel 114. The optical detection region 116 may include, as in the prior embodiment, waveguides 119, 121 that are used to direct light (e.g., UV light in waveguide 119) into the fraction collection channel 114 and collect transmitted light using waveguide 121. Of course, in other embodiments, the waveguides 119, 121 may be omitted entirely and a different optical detector may be employed that is located off-chip, for example. A light source 53 and detector 56 like that illustrated in FIG. 1 may be used. The radiation detection region 118 includes a radiation detector 62 like that described in the prior embodiment. The radiation detector 62 is located downstream with respect to the optical detection region 116.

As seen in FIG. 7A, one or more branch fraction channels 120a, 120b, 120c intersect with the fraction collection channel 114. Branch channel 120a is used as a vent channel. Branch channel 120b is used to divert the desired fraction to a collection well or reservoir 126. Branch channel 120c is used to carry a buffer wash solution contained in well or reservoir 127 to ensure that any residual product is delivered to the collection well or reservoir 126. A number of valves 122 are located in the branch fraction channels 120a, 120b, 120c and the fraction collection channel 114. These valves 122 are actuated pneumatically as is described with respect to the valves 22, 66 of the prior embodiment. The valves 122 are used to capture the desired fraction of fluid passing through the fraction collection channel 114. This may include waste or other undesired products which are then diverted to a waste well or reservoir 124. Alternatively, this may include the desired radioactive tracer compound which can then be capture and sent to a collection well or reservoir 126 via one of the branch fraction channels 120. For example, a pump 128 located on-chip may be used to pump the captured fraction into the collection well or reservoir 126. The pump 128 is also used to pump a buffer-based wash solution from the well or reservoir 127 through branch channel 120c and into branch channel 120b to reduce or minimize the amount of residual material left behind. The pump 128 may include a peristaltic pump that is formed by multiple valves 122 located in series and actuated serially to create a peristaltic pumping action. Alternatively, positive pressure may be used to push the fraction into the collection well or reservoir 126. Vacuum can also be applied to pull the fraction into the collection well or reservoir 126.

Figure 7B:
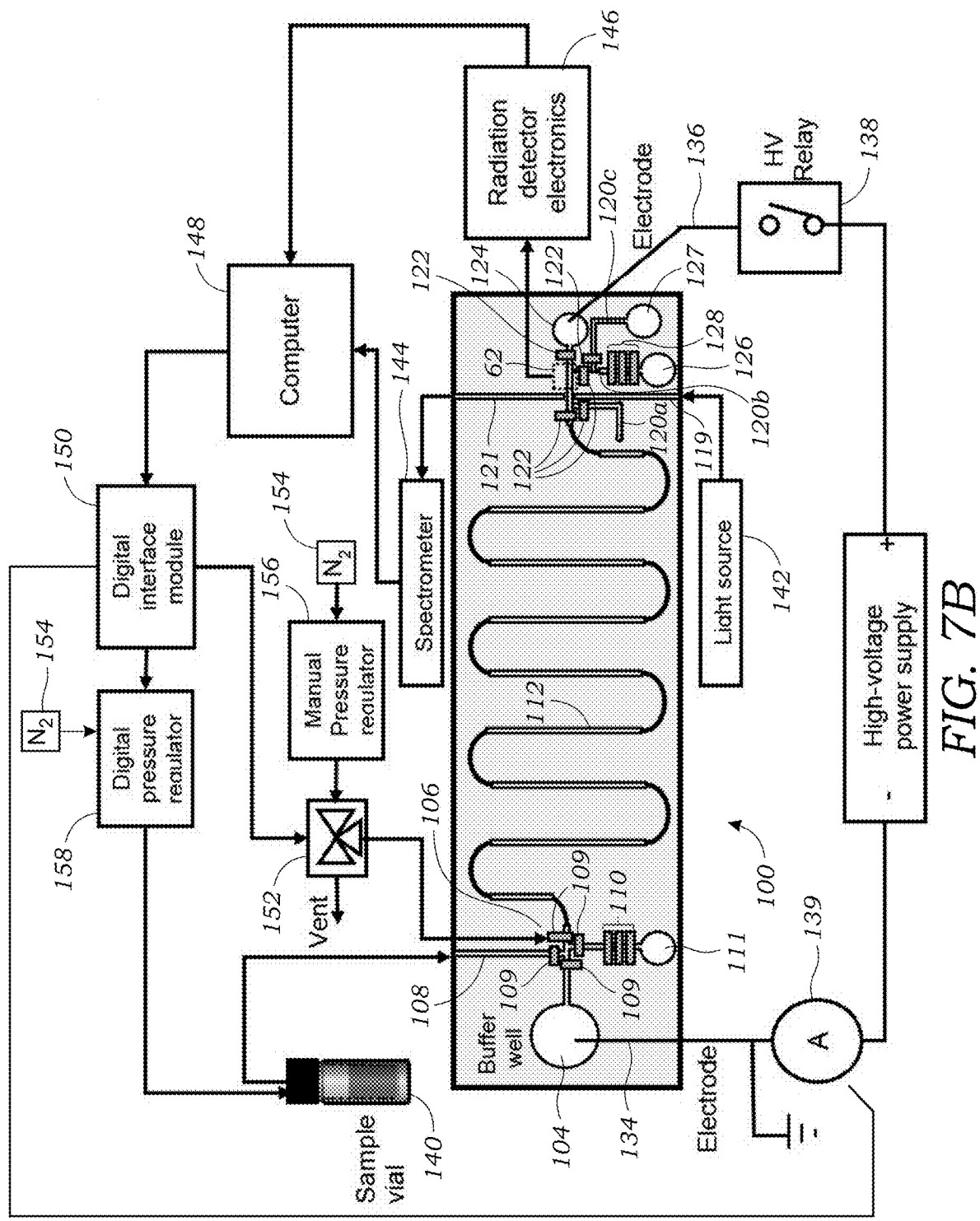
FIG. 7B illustrates one embodiment of the control system used with the integrated microfluidic CE chip.

FIG. 7B illustrates one embodiment of the control system used with the integrated microfluidic CE chip. As with the prior embodiment, a high voltage power supply 130 is used to apply a voltage between the buffer well or reservoir 104 and the waste well or reservoir 124 via electrical conductors or probes 134, 136. A high voltage relay 138 is used to turn on/off the power supply. A current meter 139 is used to monitor the current in the separation channel 112. In this example, a sample is contained in a sample vial 140 that is connected to branch channel 108 via tubing or the like. FIG. 7B illustrates a light source 142 that connects to the waveguide 119 (incoming light) and a spectrometer 144 connects to the other waveguide 121 (outgoing light). The radiation detector sensor 62 connects to off-chip detector circuitry 146. Control of the system is provided by a computer 148. The computer 148 interfaces with the off-chip detector circuitry 146 and the spectrometer 144. The computer 148 also interfaces and controls actuation of the high voltage power supply via the high voltage relay 138.

FIG. 7B further illustrates how the computer 148 interfaces with a digital interface module 150 that is used to control the valves 109, 122 located on the integrated microfluidic CE chip 100. The digital interface module 150 is also connected to current meter 139 to measure current in the separation channel 112. The digital interface module 150 may be a DAQ as is known in the art. For each valve 109, 122 (there are fifteen (15) in this embodiment), an off chip solenoid valve 152 is provided that is coupled to a pressure regulated source of gas 154 (e.g., nitrogen). A pressure regulator 156 controls the pressure provided to each solenoid valve 152. The solenoid valve 152 is coupled to the integrated microfluidic CE chip 100 via tubing or the like (not shown) to the control channels 24 so that pressurized gas, when actuated via solenoid valve 152, pressurizes the control channel 24 to actuate and close the particular valve 109, 122. Pressure is released to return the valves 109, 122 to the open state. In some embodiments, each valve 109, 122 may have its own dedicated solenoid valve 152. In other embodiments, a single solenoid valve 152 may be shared among multiple on-chip valves 109, 122. As seen in FIG. 7B, the digital interface module 150 connects to a digital pressure regulator 158 is connected to a source of pressured gas 154 to drive fluid from the sample vial 140 to the integrated microfluidic CE chip 100.

Figure 8A:
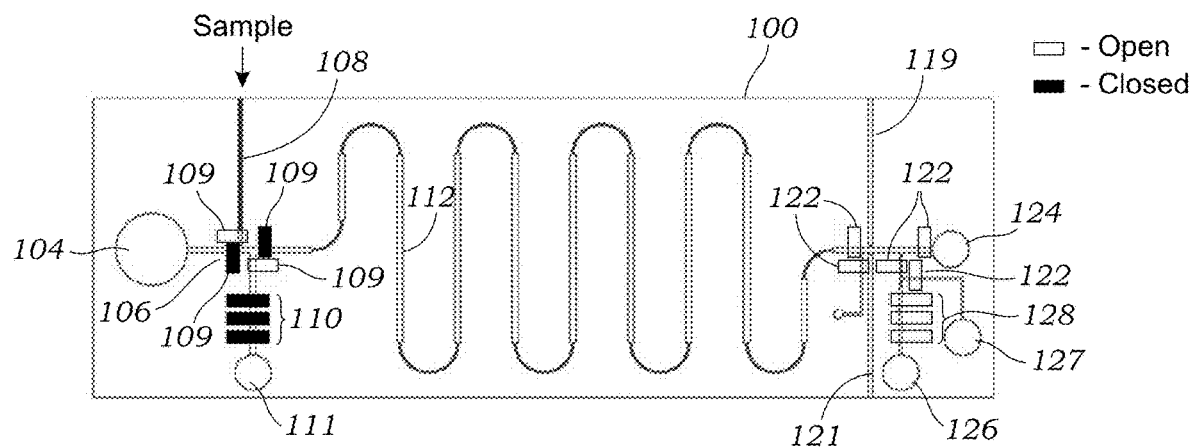
FIG. 8A illustrates a sample being input into the integrated microfluidic CE chip via a branch channel.
Figure 8B:
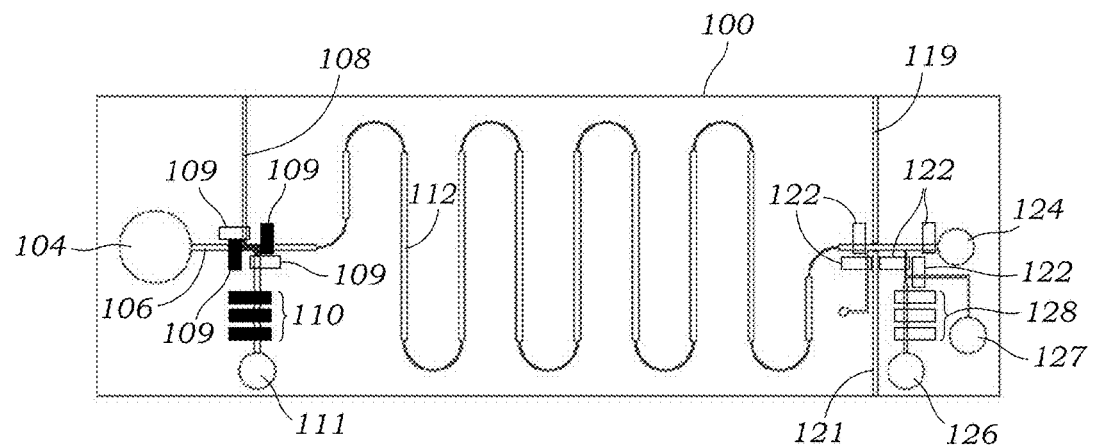
FIG. 8B illustrates a plug or volume of sample loaded into the injection channel of the integrated microfluidic CE chip.
Figure 8C:
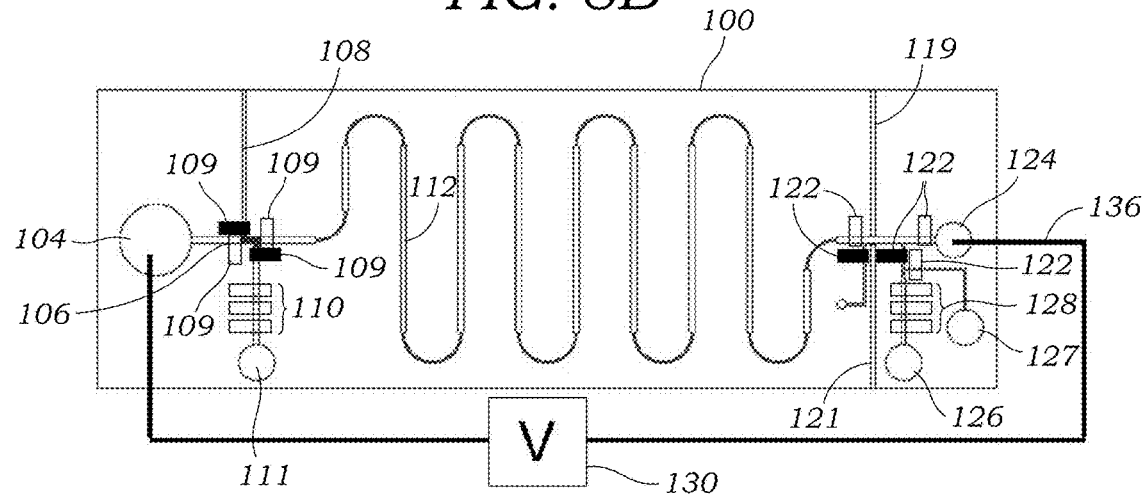
FIG. 8C illustrates the application of high voltage to the wells or reservoirs which is used to drive the channel into the separation channel.
Figure 8D:
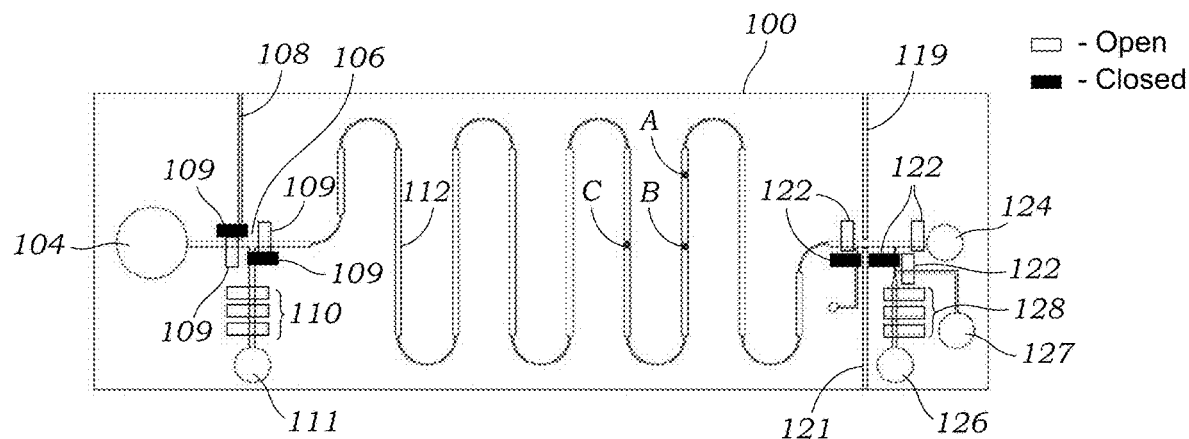
FIG. 8D illustrates the separation of the sample into fractions after passing through the separation channel. There are three fractions illustrated: A, B, and C.
Figure 8E:
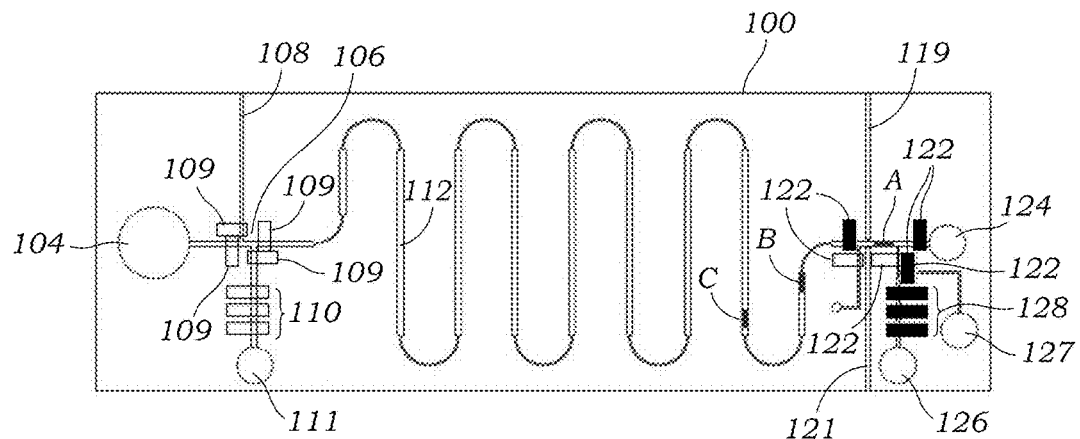
FIG. 8E illustrates the trapping of fraction A in the fraction collection channel using valves on either ends.
Figure 8F:
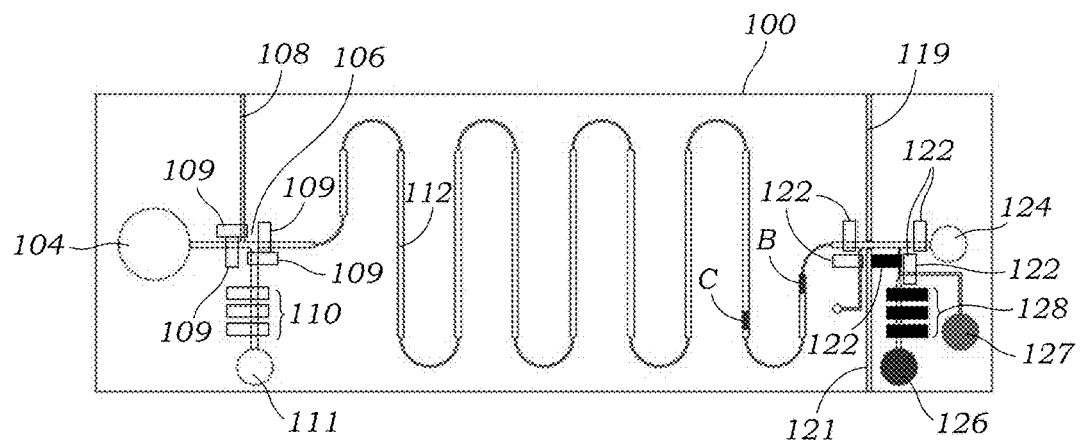
FIG. 8F illustrates the transport of fraction A into the collection well or reservoir. A wash or buffer solution is also run through the channels to minimize any residual amount or residue of fraction A.

With reference to FIGS. 8A-8F, to operate the integrated microfluidic CE chip 100, the crude sample is pumped through the sample inlet via branch fraction channel 108 into the injection channel 106 as seen in FIGS. 8A and 8B. Next, the valves 109 in the branch fraction channels 108 are closed and the CE valves 109 along the injection channel in the flow direction are opened and voltage is applied across the integrated microfluidic CE chip 100 between the well or reservoir 104 and waste well or reservoir 124 for separation of analytes as seen in FIG. 8C. FIG. 8D illustrates the separation of different fractions A, B, C in the separation channel 112. When the end of the band corresponding to the purified radioactive tracer passes through the radiation detector 62 in the radiation detection region 118, the separation voltage is turned off, the CE valves 122 along the fraction collection channel 114 are closed (FIG. 8E). The tracer is pumped off into a collection well or reservoir 126 seen in FIG. 8F. The branch fraction channel 120b is washed with wash solution from well or reservoir 127. Cerenkov imaging may be performed experimentally to determine band sizes and to optimize the design and timing parameters of the fraction collection process (e.g., when to trigger valves 122 after detection with the radiation detector 62).

Figure 9A:
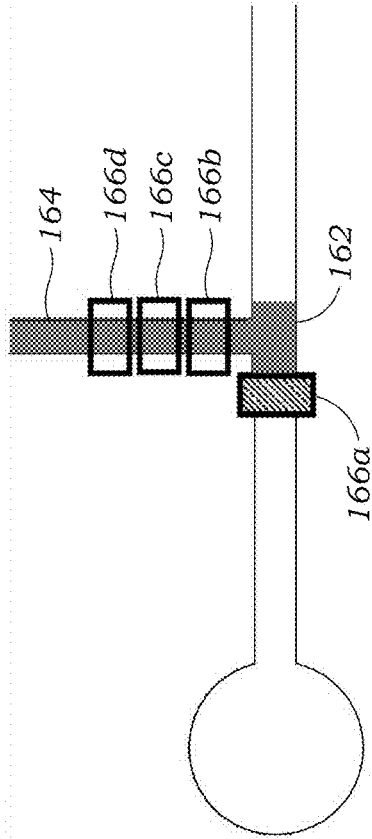
FIGS. 9A-9D illustrates one alternative embodiment of sample injection that may be employed with the microfluidic injection chip or the integrated microchip CE chip.
Figure 9B:
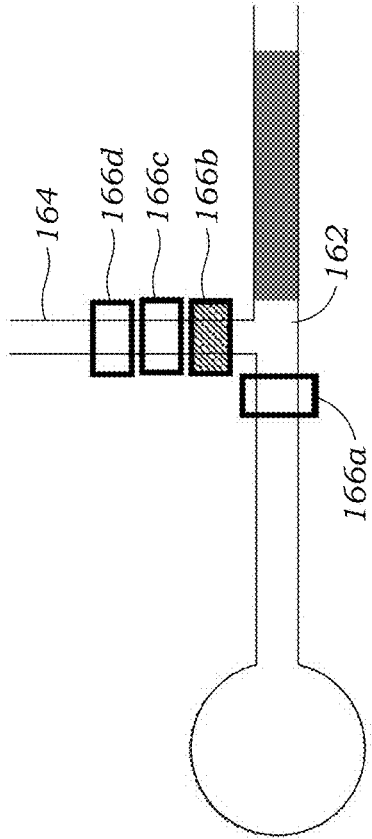
Figure 9C:
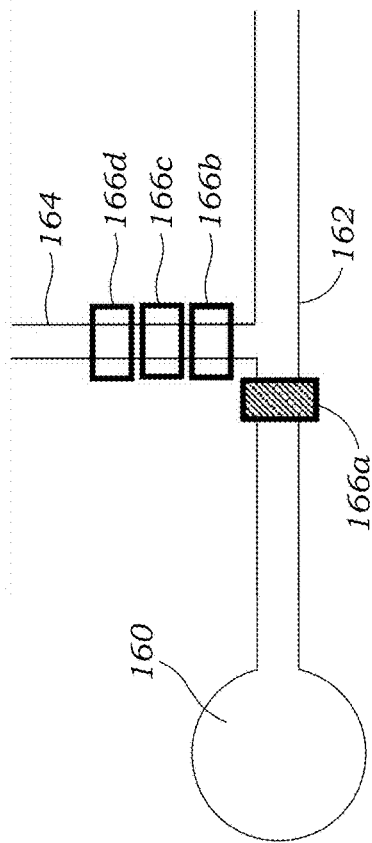
Figure 9D:
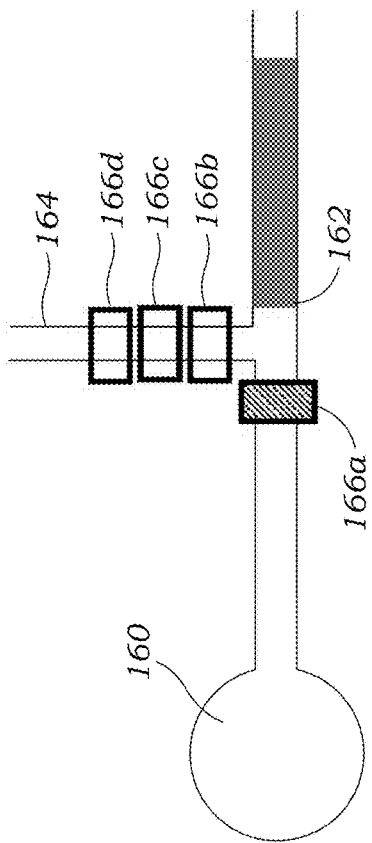

FIGS. 9A-9D illustrates one alternative embodiment of sample injection that may be employed with the microfluidic injection chip 12 or the integrated microchip CE chip 100. In this embodiment, a buffer well 160 is connected to an injection channel 162 that interfaces with a branch channel 164. A valve 166*a* is located in the injection channel 162. A plurality of valves 166*b*, 166*c*, 166*d* are located in the branch channel 164. The multiple valves 166*b*, 166*c*, 166*d* may be sequentially actuated to act as a peristaltic pump. A downstream end of the injection channel 162 leads to a capillary 30 or separation channel 112. In this alternative embodiment, valve 166*a* is closed as seen in FIG. 9A and sample is introduced into branch channel 164 as seen in FIG. 9B. Once the sample has been fully loaded into the injection channel 162 (FIG. 9C), the valve 166*a* is opened and valve 166*b* is closed (FIG. 9D). A voltage is then applied to move the fluid plug into the capillary 30 or separation channel 112.

Figure 10:
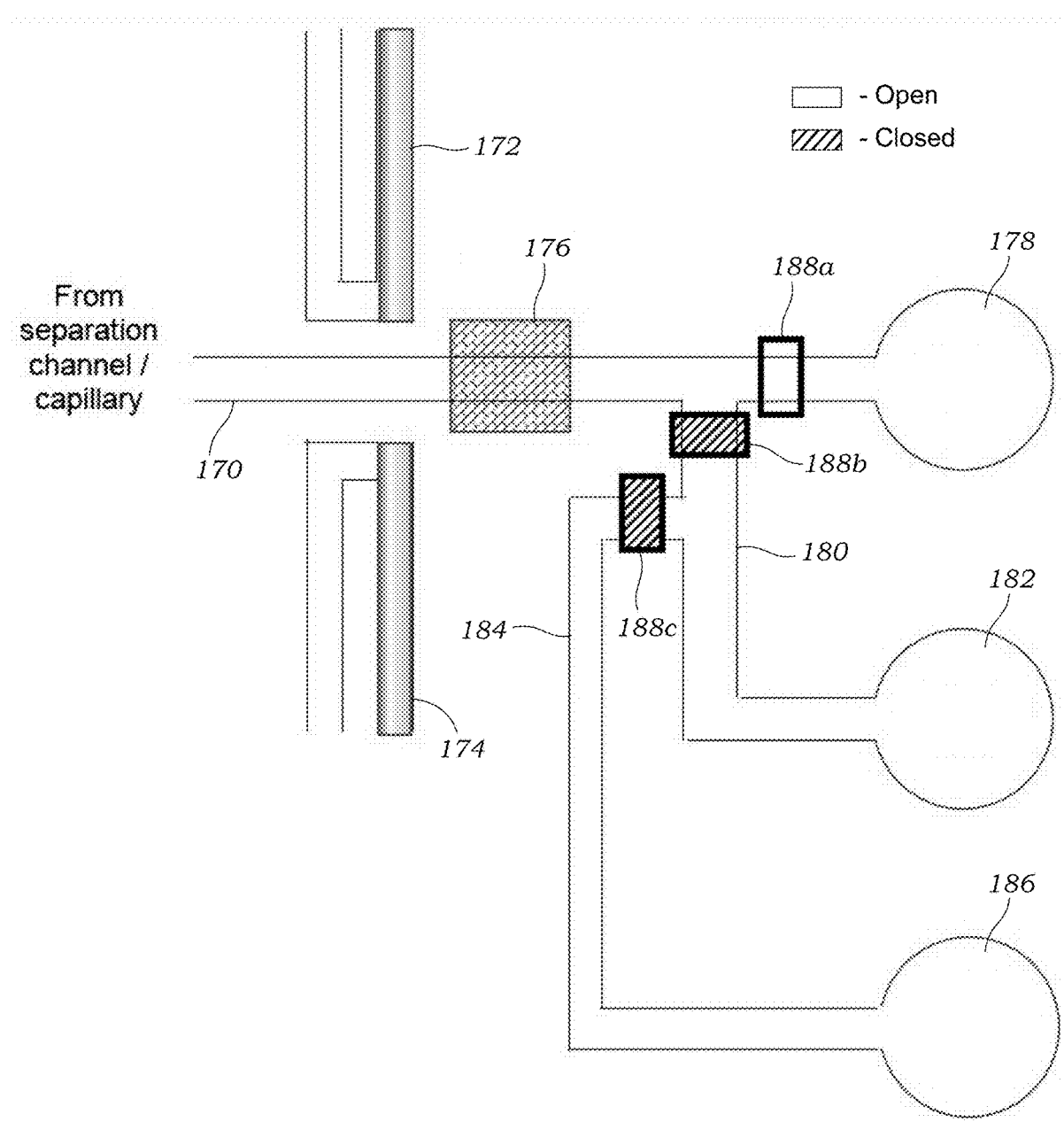
FIG. 10 illustrates one alternative embodiment of fraction collection that may be employed with the microfluidic injection chip or the integrated microchip CE chip.

FIG. 10 illustrates one alternative embodiment of fraction collection that may be employed with the microfluidic injection chip 12 or the integrated microchip CE chip 100. In this embodiment, a fraction collection channel 170 receives fractions from the capillary 30 or the separation channel 112. The fraction channel 170 includes waveguides 172, 174 that are used to optically interrogate a passing fraction as explained previously. In addition, a radiation detector 176 is located adjacent to the fraction collection channel 170 to detect radioactive fractions passing thereby. The fraction channel 170 leads to a waste well or reservoir 178. A branch channel 180 intersects with the fraction channel and leads to a collection well or reservoir 182. The collection well or reservoir 182 is pre-loaded with buffer solution to complete the electrical circuit. The branch channel 180 intersects with another branch channel 184 that terminates in a well or reservoir 186 that contains a flush or washing buffer solution. A valve 188*a* is positioned in the fraction channel along with valves 188*b*, 188*c* located in the branch channels 180, 184 respectively.

In this embodiment, valve 188*a* is opened during separation. The desired fraction peak is detected with by the radiation detector 176. The separation voltage is turned off and valve 188*a* is turned off. Valve 188*b* is opened to provide access to the collection well or reservoir 182. The separation voltage is then applied between the buffer well of the injection chip (e.g., well 18) and the collection well or reservoir 182 to collect the fraction into the collection well or reservoir 182. The separation voltage is then turned off and valve 188*b* is closed. Next, valve 188*c* is opened to provide access to the well or reservoir 186 and a voltage (at a much lower potential) is applied between the well or reservoir 186 that contains the flushing or washing solution and the collection well or reservoir 182 to ensure the that any remaining fraction is transported to the collection well or reservoir 182. In this embodiment, the same or different high voltage power supply 130 may be used to connect the wells/reservoirs 182, 186. Of course, additional conductors or probes and switching circuitry may be needed to incorporate the additional well or reservoir 186. In yet another alternative of this embodiment, the valves 188*a*, 188*b*, 188*c* are omitted and the potential is used to control the flow whereby the unused wells 178, 182, 186 are maintained at floating potential. In still another embodiment, rather than relying on a second power supply and associated switching circuitry, a pump may be used to move the fraction to the collection well or reservoir 182.

Figure 11:
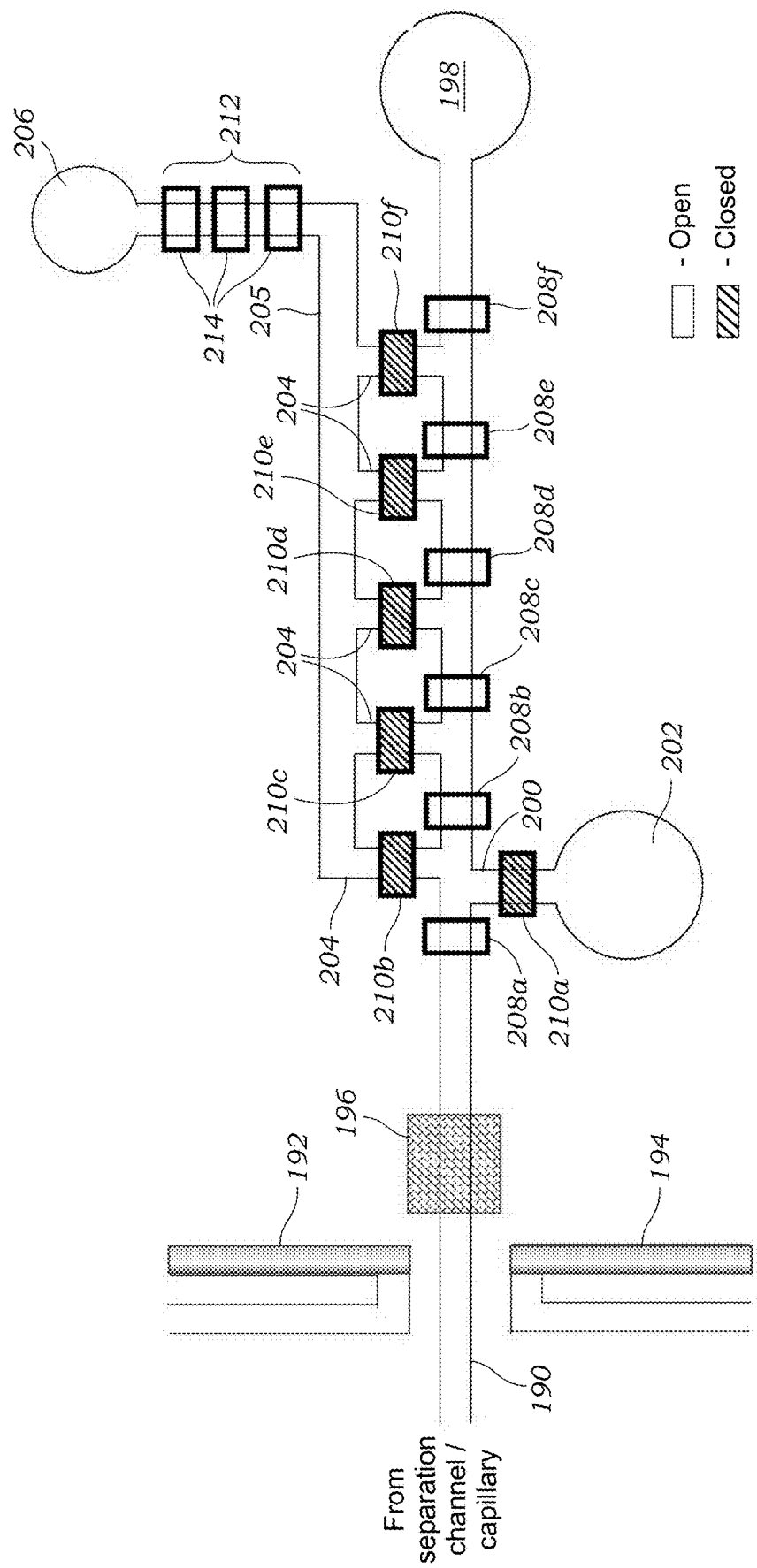
FIG. 11 illustrates one alternative embodiment of fraction collection that may be employed with the microfluidic injection chip or the integrated microchip CE chip.

FIG. 11 illustrates one alternative embodiment of fraction collection that may be employed with the microfluidic injection chip 12 or the integrated microchip CE chip 100. In this embodiment, a fraction collection channel 190 receives fractions from the capillary 30 or the separation channel 112. The fraction channel 190 includes waveguides 192, 194 that are used to optically interrogate a passing fraction as explained previously. In addition, a radiation detector 196 is located adjacent to the fraction collection channel 190 to detect radioactive fractions passing thereby. The fraction channel 190 leads to a waste cell or reservoir 198. A first branch channel 200 intersects with the fraction channel 190 and leads to a collection well or reservoir 202. A series of additional branch channels 204 connect at various downstream locations of the fraction channel 190 and combine to a common channel 205 which leads to a well or reservoir 206 that contains a wash or flush solution (e.g., buffer). A series of valves 208*a*, 208*b*, 208*c*, 208*d*, 208*e*, 208*f* are positioned along the length of the fraction collection channel 190 and separate adjacent branch channels 204. In addition, the branch channels 200, 204 each have valves 210*a*, 210*b*, 210*c*, 210*d*, 210*e*, 210*f* located therein. A pump 212 is located along the common channel 205 and may be formed using a series of valves 214 that are actuated sequentially to create peristaltic pumping action.

In the embodiment of FIG. 11, the valves 210*a*, 210*b*, 210*c*, 210*d*, 210*e*, 210*f* are closed and the valves 208*a*, 208*b*, 208*c*, 208*d*, 208*e*, 208*f* are open during the separation process (i.e., when voltage is applied). Using knowledge of the start of separation and the detection signal from the radiation sensor 196, the separation voltage is turned off and the valves located on either side of the fraction (two valves of valves 210*a*, 210*b*, 210*c*, 210*d*, 210*e*, 2100 are closed to trap the fraction. The appropriate side valves (i.e., one of valves 210*b*, 210*c*, 210*d*, 210*e*, 2100 and valve 210*a* are then opened to create a path from the well or reservoir 206 to the collection well or reservoir 202. The pump 212 is activated to flush the desired fraction into the collection well or reservoir 202. In this operation valves 208*a* and 208*f* are closed. Finally, the collection well valve 210*a* can be closed.

Note that a similar high voltage power supply 130 and computer controlled valving process may be used for the embodiment that uses the integrated microchip CE chip 100. For separation, voltage is applied between the ends of the injection region and the fraction collection region to drive the CE process (e.g., in wells or reservoirs 104, 124). Electrodes may be also be patterned or formed within the channels of the microfluidic CE chip which can be connected to the voltage source during operation of the device.

The fully integrated microchip CE chip 100 also gives greater flexibility in channel geometry and increased options for temperature control to reduce the impact of Joule heating (e.g., integration of recirculating coolant channels; interfacing with thermoelectric cools, heat pipes or pool boiling systems). The chip 100 may be fabricated from polydimethylsiloxane (PDMS) via standard molding processes. The fully integrated microchip CE chip is ultimately preferred vs the "hybrid" capillary format as it is more compact (reduces need for radiation shielding) and will be easier to interface with upstream and downstream components. It may also cost less to fabricate because assembly steps (of separate chips and capillary) is not required.

In one embodiment, the radiation detector 62 may be changed or swapped with different types of radiation detectors 62 so that a single microfluidic detector chip 40 or integrated microchip CE chip 100 can be used to detect different tracers. Different tracers, particularly different tracers labeled with different isotopes, may use different types of radiation detectors 62. The radiation detectors 62 may be secured to the microfluidic detector chip 40 or integrated microchip CE chip 100 via an adhesive layer which can be broken by pulling the radiation detector 62 away from the chip 40, 100. In other embodiments, the radiation detectors 62 does not require any adhesive and is easily separable from the microfluidic detector chip 40 or integrated microchip CE chip 100. For example, the chip 40, 100 may be disposable and the radiation detector 62 is reusable.

While embodiments of the present invention have been shown and described, various modifications may be made without departing from the scope of the present invention. For example, in one alternative embodiment, the optical waveguides may transmit light of a different wavelength than UV light. In yet another alternative, the optical waveguides may be replaced with an in-channel electrode(s) that utilize pulsed amperometric detection (PAD) that are known to those skilled in the art. In yet another alternative, the optical waveguides may be replaced with a non-contact sensor such as capacitively-coupled contactless detectors (C4D) that are known to those skilled in the art. Some compounds or species are hard to identify with UV light spectrophotometry. The invention, therefore, should not be limited, except to the following claims, and their equivalents.

What is claimed is:

1. A device for purifying a radiochemical compound comprising:

a microfluidic injection chip comprising an injection channel having an outlet at one end and a well or reservoir at an opposing end, the injection channel being configured to receive a volume of unpurified sample containing the radiochemical compound, the microfluidic injection chip comprising a plurality of intersecting microfluidic branch channels, wherein a plurality of microfluidic valves are positioned along the plurality of intersecting microfluidic branch channels and along the injection channel, wherein the plurality of microfluidic valves positioned along the injection channel selectively define an injection volume within the range of 1-10 μL;

a capillary connected at a first end to the outlet of the microfluidic injection chip;

a microfluidic detector chip connected to a second end of the capillary, the microfluidic detector chip comprising a fraction collection channel coupled at one end to the second end of the capillary and fluidically coupled at another end to a waste well or reservoir and one or more branch fraction channels intersecting with the fraction collection channel, wherein a first portion of the fraction collection channel defines an optical detection region, and wherein a second portion of the fraction collection channel located downstream of the optical detection region defines a radiation detection region containing a solid-state radiation detector, wherein a plurality of valves are positioned along the one or more branch fraction channels and along the fraction collection channel;

a high voltage power supply having a first conductor in contact with the well or reservoir of the microfluidic injection chip and a second conductor in contact with the waste well or reservoir of the microfluidic detector chip;

wherein the solid-state radiation detector is located within a recess disposed in the microfluidic detector chip in the radiation detection region; and wherein actuation of the high voltage power supply drives the injection volume into the capillary for separation and detection in the microfluidic detector chip without the aid of any separate pump.

2. The device of claim 1, wherein the optical detection region comprises one or more optical waveguides disposed in the microfluidic detector chip across a width or length of the fraction collection channel wherein the one or more optical waveguides are coupled to a source of light and a detector.

3. The device of claim 1, wherein the solid-state radiation detector is bonded to the microfluidic detector chip and is located less than 500 μm from the fraction collection channel.

4. The device of claim 3, wherein the solid-state radiation detector comprises an avalanche photodiode (APD).

5. The device of claim 1, wherein the solid-state radiation detector comprises a gamma ray detector.

6. The device of claim 1, wherein the capillary has an internal diameter (ID) within a range of 100 μm to 1 mm.

7. The device of claim 1, wherein the fraction collection channel comprises a serpentine section comprising a plurality of tapered serpentine turns and wherein the solid-state radiation detector is located adjacent to the serpentine section.

8. The device of claim 1, further comprising a collection well or reservoir located on the microfluidic detector chip and coupled to one of the one or more branch fraction channels.

* * * * *